US012606806B2

(12) United States Patent
Beeram et al.

(10) Patent No.: US 12,606,806 B2
(45) Date of Patent: Apr. 21, 2026

(54) **NUCLEIC ACIDS, VECTORS, HOST CELLS AND METHODS FOR PRODUCTION OF FRUCTOSYLTRANSFERASE FROM *ASPERGILLUS JAPONICUS***

(71) Applicant: Revelations Biotech Pvt Ltd, Hyderabad (IN)

(72) Inventors: Ravi Chandra Beeram, Hyderabad (IN); Dipanwita Sinha, Hyderabad (IN); Bharath Babu Musuku, Secunderabad (IN); Chiranjeevi Are, Hyderabad (IN); Deepika Kumar, Hyderabad (IN)

(73) Assignee: Revelations Biotech Pvt Ltd, Hyderabad (IN)

( * ) Notice: Subject to any disclaimer, the term of this patent is extended or adjusted under 35 U.S.C. 154(b) by 783 days.

(21) Appl. No.: 17/779,012

(22) PCT Filed: Nov. 27, 2020

(86) PCT No.: PCT/IN2020/050986
§ 371 (c)(1),
(2) Date: May 23, 2022

(87) PCT Pub. No.: WO2021/106017
PCT Pub. Date: Jun. 3, 2021

(65) Prior Publication Data
US 2023/0220358 A1     Jul. 13, 2023

(30) Foreign Application Priority Data

Nov. 27, 2019   (IN) .............................. 201941048679

(51) Int. Cl.
*C12N 9/10* (2006.01)
*C12N 1/145* (2026.01)
*C12N 15/80* (2006.01)

(52) U.S. Cl.
CPC ........... *C12N 9/1051* (2013.01); *C12N 1/145* (2021.05); *C12N 15/80* (2013.01);
(Continued)

(58) Field of Classification Search
CPC ...... C12N 9/1051; C12N 1/145; C12N 15/80; C12N 2523/00; C12Y 204/01009;
(Continued)

(56) References Cited

U.S. PATENT DOCUMENTS 7,141,547 B2 * 11/2006 Rosen ........................ A61P 9/14
                                                              514/6.9
8,936,917 B2 *  1/2015 Wang ................... C07K 16/462
                                                              435/320.1
(Continued)

FOREIGN PATENT DOCUMENTS

WO      WO2003060071 A2     7/2003
WO      WO2008048378 A2     4/2008
(Continued)

OTHER PUBLICATIONS

Yu et al. Batch isolation of novel sequences targeting regions of rapid viral variations. Indian Journal of Animal Sciences. 2012, 82 (7): 665-670 (Year: 2012).*
Gan et al. D181A Site-Mutagenesis Enhances Both the Hydrolyzing and Transfructosylating Activities of BmSUC1, a Novel Î²-Fructofuranosidase in the Silkworm *Bombyx mori*. Int J Mol Sci. Feb. 28, 2018;19(3):683 (Year: 2018).*
(Continued)

*Primary Examiner* — Manjunath N Rao
(74) *Attorney, Agent, or Firm* — Mandar A. Joshi; Bret E. Field; Bozicevic, Field & Francis LLP

(57) ABSTRACT
The present invention provides nucleic acids, vectors, host cells and methods for production of fructosyltransferase from *Aspergillus japonicus*. The invention represents an advancement in the field of genetic engineering and provides methods for obtaining high yield of a novel recombinant
(Continued)

fructosyltransferase encoded by ft gene of *Aspergillus japonicus* as a secreted protein.

15 Claims, 7 Drawing Sheets

Specification includes a Sequence Listing.

(52) U.S. Cl.
CPC ................. *C12Y 204/01009* (2013.01); *C12Y 204/01099* (2013.01); *C07K 2319/02* (2013.01); *C12N 2523/00* (2013.01)

(58) Field of Classification Search
CPC ........ C12Y 204/01099; C07K 2319/02; C07K 2319/50; C12P 19/18
See application file for complete search history.

(56) References Cited

U.S. PATENT DOCUMENTS

| | | | | |
|---|---|---|---|---|
| 10,131,927 B2 * | 11/2018 | Pérez | ...................... | A23L 29/30 |
| 2017/0298332 A1 * | 10/2017 | Trollope | .............. | A23L 33/125 |

FOREIGN PATENT DOCUMENTS

| | | |
|---|---|---|
| WO | WO2016051386 A1 | 4/2016 |
| WO | WO2016073562 A1 | 5/2016 |

OTHER PUBLICATIONS

Oxford English Dictionary, s.v. "harbour | harbor (n. 1), sense 1-3" Dec. 2024, https://doi.org/10.1093/OED/2052342070. (last accessed Feb. 10, 2025) (Year: 2024).*

GenBank ID ADK46938 (Year: 2011).*

NPL GenBank ID: AFJ80404 (Year: 2001).*

NPL GenBank ID JN088769 (Year: 2013).*

NPL Blast UDJWRU6V114-Alignment 17779012 SEQ ID No. 1 VS ADK46938 (Year: 2025).*

NPL GenBank WP_003803118 (Year: 2024).*

Van Wyk et al., Identification of the gene for β-fructofuranosidase from Ceratocystis moniliformis CMW 10134 and characterization of the enzyme expressed in *Saccharomyces cerevisiae*, BMC Biotechnology 2013, 13:100, pp. 1-11.

NCBI database: "fructosyltransferase [Aspergillus japonicus]", GenBank accession No. ADK46938.1, Mar. 1, 2011.

Chuankhayan et al., Crystal Structures of Aspergillus japonicus Fructosyltransferase Complex with Donor/Acceptor Substrates Reveal Complete Subsites in the Active Site for Catalysis, J Biol Chem, Jul. 23, 2010; 285(30):23251-64.

Zhang et al., Molecular cloning and over-expression of a fructosyltransferase from Aspergillus niger QU10, Chinese Journal of Biotechnology, Apr. 25, 2015, 31(4): 512-522.

Juturu et al., Heterologous Protein Expression in Pichia pastoris: Latest Research Progress and Applications, ChemBioChem, Jan. 4, 2018, 19(1):7-21.

* cited by examiner

```
Native      ATGAAGCTCACCACTACCACCCTGGCGGCTCGCCACCGGTGCAGCAGCAGCAGAAGCCTCA
Modified    ATGAAATTGACTACTACTACTTTGGCTTTGGCTACTGGTGCTGCTGCTGCTGAAGCTTCT
            *****.* ** ***** ** **** * ** ** *****;**;**;**;***** **;

Native      TACCACCTGGACACCACGGCCCCGCCGCCGACCAACCTCAGCACCCTCCCCAACAACACC
Modified    TACCATTTGGATACTACTGCTCCACCTCCAACTAATTTGTCTACTTTGCCTAACAACACT
            ***** **** ** ** ** **,** **,** ** * ; ** ** *******

Native      CTCTTCCACCTGTGGCGGCCGCGCGCGCACATCCTGCCCGCCGAGGGCCAGATCGGCGAC
Modified    TTGTTTCATTGTGGAGACCAAGAGCCCATATTTTGCCAGCTGAAGGTCAAATTGGAGAT
            * ** ** ** *****,*.**,,*.** ** ** ****,** **,** **,** **,**

Native      CCCTGCGCGCACTACACCGACCCATCCACCGGCCTCTTCCACGTGGGGGTTCCTGCACGAC
Modified    CCATGTGCTCACTACACTGATCCATCTACTGGTTTGTTTCATGTTGGTTTCTTGCACGAT
            **,** ** ******** ** ***** ** ** * ** ** ** ** *** *******

Native      GGGGACGGCATCGCGGGCGCCACCACGGCCAACCTGGCCACCTACACCGACACCTCCGAT
Modified    GGAGATGGTATTGCTGGTGCTACTACTGCTAATTTGGCTACTTATACTGATACTTCTGAT
            ** ** ** ** ** ** ** ** ** ** **** ** ** ** ** ** ** ***

Native      AACGGGAGCTTCCTGATCCAGCCGGGCGGGAAGAACGACCCCGTCGCCGTGTTCGACGGC
Modified    AACGGTTCTTTCTTGATTCAACCAGGTGGTAAAAACGATCCAGTTGCTGTTTTCGATGGT
            ***** ; *** **** **,**,** ** **,***** **,** ** ** ***** **

Native      GCCGTCATCCCCGTCGGCGGTCAACAACACCCCCACCTTACTCTACACCTCCGTCTCCTTC
Modified    GCTGTTATTCCTGTTGGTGTTAACAATACTCCAACTTTGTTGTACACTTCTGTTCTTTC
            ** ** ** ** ** ** ** ***** ** **,** **, * ***** ** ** ** ***

Native      CTGCCCATCCACTGGTCCATCCCCCTACACCCGCGGCAGCGAGACGCAGTCGTTGGCCGTC
Modified    TTGCCTATTCATTGGTCTATTCCATATACTAGAGGTTCTGAAACTCAATCTTTGGCTGTT
            **** ** ** ***** ** **,** ** ,*,**,; ** **,** **,** ***** **

Native      GCGGCGGACGGCGGCCGCCGCTTCGACAAGCTCGACCAGGGCCCCGTCATCGCCGACCAC
Modified    GCTAGAGATGGTGGTAGAAGATTCGATAAATTGGATCAAGGTCCTGTTATTGCTGATCAC
            **,*,** ** ** **,*,* ***** **, * ** **,** ** ** ** ** ***

Native      CCCTTCGCCGTCGACGTCACCGCCTTCCGCGCGATCCGTTTGTCTTCCGCAGTGCCAGGTTG
Modified    CCATTGCTGTTGATGTTACTGCTTTTCAGAGATCCTTTTGTTTTTAGATCCGCTAGATTG
            **,** ** ** ** ** ** ** ***,* ***** ***** ** .*,; ** **,***

Native      GATGTGCTGCTGTCGTTGGATGAGGAGGTGGCGCGGAATGAGACGGCCGTGCAGCAGGCT
Modified    GATGTTTTGTTGTCTTTGGATGAAGAGGTTGCTAGAAATGAGACTGCTGTTCAACAAGCT
            ***** ** **** ********,***** **,* *,******** ** ** **,** ,***

Native      GTCGATGGCTGGACCGAGAAGAACGCCCCCTGGTATGTCGCGGTTTCTGGCGGGGTGCAC
Modified    GTTGATGGTTGGACTGAAAAGAACGCTCCTTGGTACGTTGCTGTTTCTGGTGGTGTTCAT
            ** ***** ***** **,********* ** ***** ** ** ******** ** ** **

Native      GGCGTCGGGCCCGCGCAGTTCCTCTACCGCCAGAACGGCGGGAACGCCTTCCGAGTTCCAG
Modified    GGTGTTGGTCCAGCTCAATTTTTTGTATAGACAAAACGGTGGTAATGCTTCTGAATCCAA
               , ,  * **,*,,*   * ,*****, Native      TACTGGGAGTACCTCGGGGAGTGGTGGCAGGAGGCGACCAACTCCAGCTGGGCGACGAG
Modified    TACTGGGAATATTTGGGTGAATGGTGGCAAGAAGCTACTAATTCTTCTTGGGGAGATGAG
            *******,.** * ** **,********,.**,** ** ** **; *****,** ***

Native      GGCACCTGGGCCGGGCGCTGGGGGTTCAACTTCGAGACGGGGAATGTGCTCTTCCTCACC
Modified    GGTACTTGGGCTGGTAGATGGGGGTTTTAACTTCGAAACTGGTAACGTTTGTTTTTGACT
            ** ** ***** **,*.***** ** ******** ** ** ** **,* *** * ***

Native      GAGGAGGGCCATGACCCCCAGACGGGCGAGGTGTTCGTCACCCTCGGCACGGAGGGGTCT
Modified    GAAGAGGGTCACGATCCACAAACTGGAGAGGTTTTCGTTACTTTGGGTACTGAAGGTTCT
            **,***** ** ** **,** **,** ** ** ** ***** ** * ** ** **,** ***

Native      GGCCTGCCCATCGTGCCGCAGGTCTCCAGTATCCACGATATGCTGTGGGCGGCGGGTGAG
```

FIG. 1

```
Modified    GGTTTGCCTATTGTTCCACAAGTTTCTTCTATTCACGATATGTTGTGGGCTGCTGGTGAA
            ** .**** ** ** **.**.** ** ; *** ******** ******* ** *****.

Native      GTCGGGGTGGGCAGTGAGCAGGAGGGTGCCAAGGTCGAGTTCTCCCCCTCCATGGCCGGG
Modified    GTTGGTGTTGGTTCTGAACAAGAGGGTGCTAAGGTTGAATTTTCTCCTTCTATGGCTGGT
            ** ** ** ** ; ***.**.******* ***** **.** ** ** ** ***** **

Native      TTTCTGGACTGGGGGTTCAGCGCCTACGCTGCGGCGGGCAAGGTGCTGCCGGCCAGCTCG
Modified    TTCTTGGATTGGGGGTTTCTCTGCTTACGCTGCTGCTGGTAAAGTTTTGCCAGCTTCTTCT
            ** .**** ***** ***; ** ******** ** ** **.** **** **.; **

Native      GCGGTGTCGAAGACCAGCGGCGTGGAGGTGGATCGGTATGTCTCGTTCGTCTGGTTGACG
Modified    GCTGTTTCTAAAACTTCTGGTGTTGAGGTTGATAGATACGTTTCTTTTGTTTGGTTGACT
            ** ** ** **.** ; ** ** ***** ***.*.** ** ** ** ** *******

Native      GGCGACCAGTACGAGCAGGCGGACGGGTTCCCCACGGCTCAGCAGGGGTGGACGGGGTCG
Modified    GGAGATCAATATGAACAAGCTGATGGTTTCCCTACTGCTCAACAAGGTTGGACTGGTTCT
            **.** **.** **.** **.** ** ** ***** ** *****.**.** ***** ** **

Native      CTGCTGCTGCCGCGCGAGCTGAAGGTGCAGACGGTGGAGAACGTCGTCGACAACGAGCTG
Modified    TTGTTGTTGCCAAGAGAATTGAAAGTTCAAACTGTTGAGAACGTTGTTGATAATGAATTG
             ** ** ****.**.*.**. **** **.** **.** ** ******** ** ** ** **. **

Native      GTGCGCGAGGAGGGCGTGTCGTGGGTGGTGGGGGAGTCGGACAACCAGACGGCCACGCTT
Modified    GTTAGAGAAGAGGGTGTTTCTTGGGTTGTTGGAGAGTCTGATAATCAAACTGCTACTTTG
            ** .*.**.***** ** ** ***** ** **.***** ** **.** ** ** **  *

Native      CGCACGCTGGGGATCACGATCGCCCGGGAGACCAAGGCGGCCCTGCTGGCCAACGGCTCG
Modified    AGAACTTTGGGTATTACTATTGCTAGAGAAACTAAGGCTGCTTTGTTGGCTAACGGTTCT
            .*.**  **** ** ** ** ** .*.**.** ***** ** ** **** ***** **

Native      GTGACCGCGGAGGAGGACCGCACGCTGCAGACGGCGGCCGTCGTGCCGTTCGCGCAATCG
Modified    GTTACTGCTGAAGAGGATAGAACTTTGCAAACTGCTGCTGTTGTTCCTTTCGCTCAATCT
            ** ** ** **.***** .*.** **** .** ** ** ** ** ***** *****

Native      CCGAGCTCCAAGTTCTTCGTGCTGACGGCCCAGCTGGAGTTCCCCGCGAGCGCGCGCTCG
Modified    CCATCTTCTAAGTTTTTCGTTTTTGACTGCTCAATTGGAGTTTCCTGCTTCTGCTAGATCC
            **.; ** ***** *****  **** ** **. ******* ** ** ; ** .*.**

Native      TCCCCGCTCCAGTCCGGGTTCGAAATCCTGGCGTCGGGAGCTGGAGCGCACGGCCATCTAC
Modified    TCTCCATTGCAATCTGGTTTCGAAATTTTTGGCTTCTGAATTGGAGAGAACTGCTATCTAC
            ** **. * **.** ** ** ********  **** ** **. *****.*.** ** ******

Native      TACCAGTTCAGCAACGAGTCGCTGGTCGTCGACCGCAGCCAGACCAGTGCGGCGGCGCCC
Modified    TACCAATTCTCTAACGAGTCTTTTGGTTGTTGATAGATCCCAAACTTCTGCTGCTGCTCCT
            *****.***; ******** **** ** ** .*.; ***.** ; *** ** ** **

Native      ACGAACCCCGGGCTGGATAGCTTTACTGAGTCCGGCAAGTTGCGGTTGTTCGACGTGATC
Modified    ACTAACCCAGGTTTTGGATTCTTTTACTGAGTCTGGTAAATTGAGATTGTTCGATGTTATC
            ** *****.** *****; ********** ** **.***.*.******** ** ***

Native      GAGAACGGCCAGGAGCAGGTCGAGACGTTGGATCTCACTGTCGTCGTGGATAACGCGGTT
Modified    GAAAACGGTCAAGAACAAGTTGAGACTTTGGATTTGACTGTTGTTGTTGATAACGCTGTT
            **.***** **.**.**.** ***** ****** * ***** ** ** ******** ***

Native      GTCGAGGTGTATGCCAACGGGCGCTTTGCGTTGAGCACCTGGGCGAGATCGTGGTACGAC
Modified    GTTGAAGTTTACGCTAATGGTAGATTTGCTTTGTCTACTTGGGCTAGATCCTGGTACGAT
            ** **.** ** ** ** **.*.***** ***; ** ***** ***** ********

Native      AACTCCACCCAGATCCGCTTCTTCCACAACGGCGAGGGCGAGGTGCAGTTCAGGAATGTC
Modified    AACTCTACTCAAATCAGATTTTTTCCACAATGGTGAAGGAGAGGTTCAATTCAGAAACGTT
            ***** ** **.***.*.** ******** ** **.**.***** **.*****.** **

Native      TCCGTGTCGGAGGGGCTCTATAACGCCTGGCCGGAGAGAAAGTGA
Modified    TCTGTTTCTGAGGGTTTTGTATAACGCTTGGCCAGAAAGAAAGTGA
            ** ** ** ***** * ******** *****.**.*********
```

<div align="center">FIG. 1 (CONT.)</div>

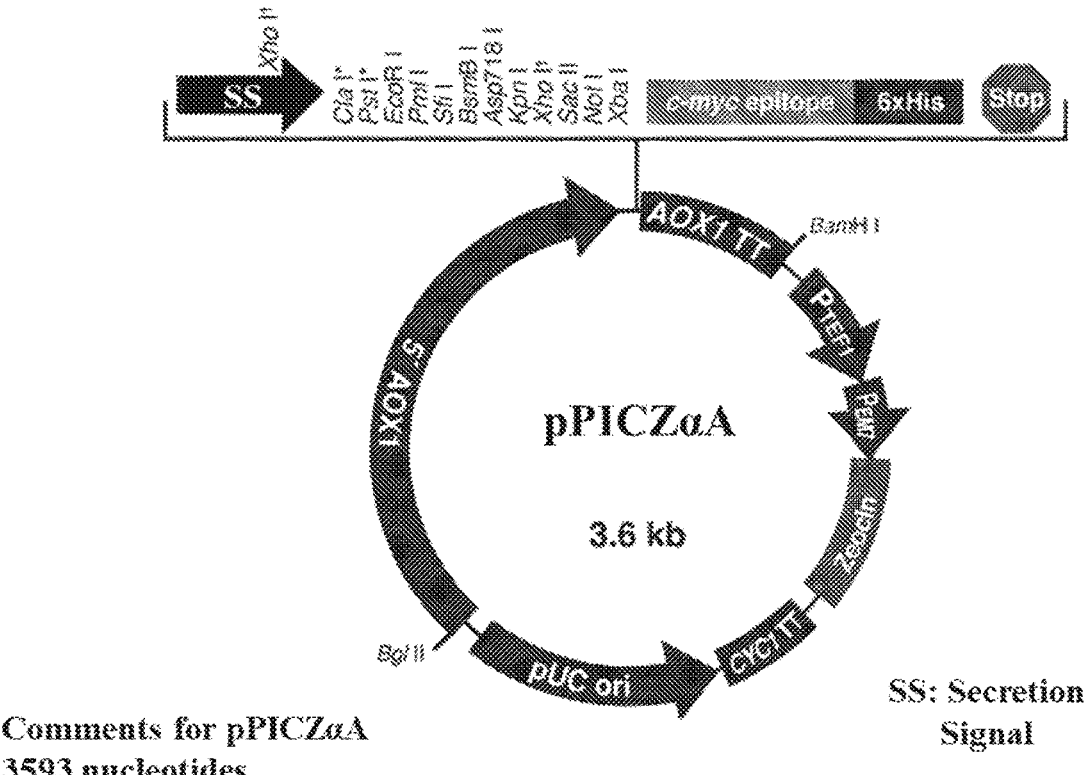

Comments for pPICZαA
3593 nucleotides

5′ AOX1 promoter region: bases 1-941
5′ AOX1 priming site: bases 855-875
a-factor signal sequence: bases 941-1207
Multiple cloning site: bases 1208-1276
c-myc epitope: bases 1275-1304
Polyhistidine (6xHis) tag: bases 1320-1337
3′ AOX1 priming site: bases 1423-1443
AOX1 transcription termination region: bases 1341-1682
TEF1 promoter: bases 1683-2093
EM7 promoter: bases 2095-2162
Sh ble ORF: bases 2163-2537
CYC1 transcription termination region: bases 2538-2855
pUC origin: bases 2866-3539 (complementary strand)

SS: Secretion
Signal

FIG. 2

U: Uncut
C: Cut with XhoI/SacII

*A. Japonicus*
*Frucosyltransferase*
*(ft)*, 1980 bp

M: protein marker
CN: colony number

I:   induced

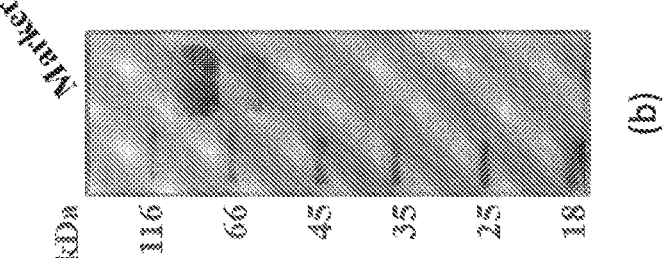
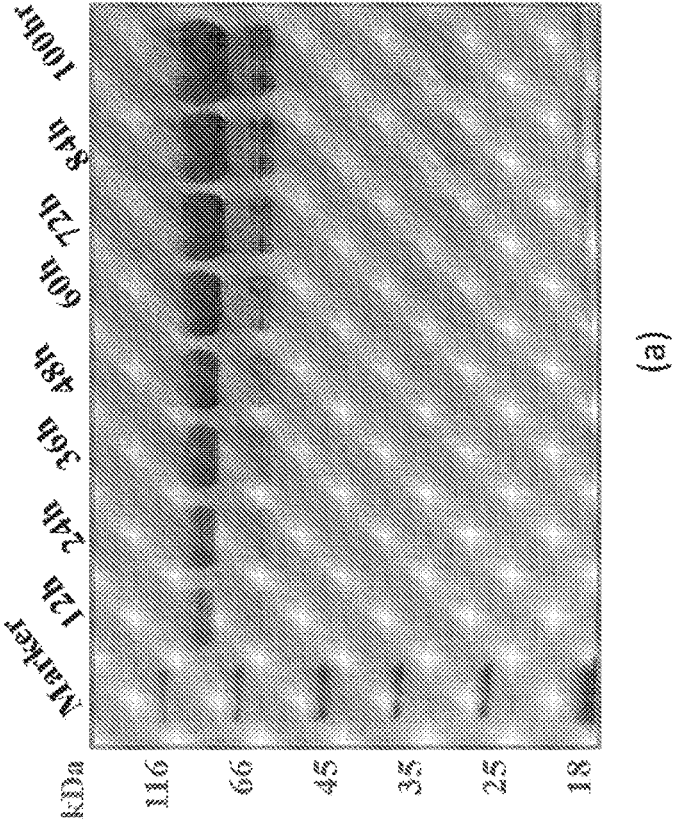
FIG. 5

Glucose standard curve (2.5 ml)

$y = 0.2521x - 0.0719$
$R^2 = 0.9939$

OD @ 540 nm

µmoles of Glucose

Standards     Formed FOS

```
                         SEQUENCE LISTING

<160> NUMBER OF SEQ ID NOS: 27

<210> SEQ ID NO 1
<211> LENGTH: 654
<212> TYPE: PRT
<213> ORGANISM: Aspergillus japonicus

<400> SEQUENCE: 1

Met Lys Leu Thr Thr Thr Thr Leu Ala Leu Ala Thr Gly Ala Ala Ala
1               5                   10                  15

Ala Glu Ala Ser Tyr His Leu Asp Thr Thr Ala Pro Pro Pro Thr Asn
            20                  25                  30

Leu Ser Thr Leu Pro Asn Asn Thr Leu Phe His Leu Trp Arg Pro Arg
        35                  40                  45

Ala His Ile Leu Pro Ala Glu Gly Gln Ile Gly Asp Pro Cys Ala His
    50                  55                  60

Tyr Thr Asp Pro Ser Thr Gly Leu Phe His Val Gly Phe Leu His Asp
65                  70                  75                  80

Gly Asp Gly Ile Ala Gly Ala Thr Thr Ala Asn Leu Ala Thr Tyr Thr
                85                  90                  95

Asp Thr Ser Asp Asn Gly Ser Phe Leu Ile Gln Pro Gly Gly Lys Asn
            100                 105                 110

Asp Pro Val Ala Val Phe Asp Gly Ala Val Ile Pro Val Gly Val Asn
        115                 120                 125

Asn Thr Pro Thr Leu Leu Tyr Thr Ser Val Ser Phe Leu Pro Ile His
    130                 135                 140

Trp Ser Ile Pro Tyr Thr Arg Gly Ser Glu Thr Gln Ser Leu Ala Val
145                 150                 155                 160

Ala Arg Asp Gly Gly Arg Arg Phe Asp Lys Leu Asp Gln Gly Pro Val
                165                 170                 175

Ile Ala Asp His Pro Phe Ala Val Asp Val Thr Ala Phe Arg Asp Pro
            180                 185                 190

Phe Val Phe Arg Ser Ala Arg Leu Asp Val Leu Leu Ser Leu Asp Glu
        195                 200                 205

Glu Val Ala Arg Asn Glu Thr Ala Val Gln Gln Ala Val Asp Gly Trp
    210                 215                 220

Thr Glu Lys Asn Ala Pro Trp Tyr Val Ala Val Ser Gly Gly Val His
225                 230                 235                 240

Gly Val Gly Pro Ala Gln Phe Leu Tyr Arg Gln Asn Gly Gly Asn Ala
                245                 250                 255

Ser Glu Phe Gln Tyr Trp Glu Tyr Leu Gly Glu Trp Trp Gln Glu Ala
            260                 265                 270

Thr Asn Ser Ser Trp Gly Asp Glu Gly Thr Trp Ala Gly Arg Trp Gly
            275                 280                 285

Phe Asn Phe Glu Thr Gly Asn Val Leu Phe Leu Thr Glu Glu Gly His
    290                 295                 300

Asp Pro Gln Thr Gly Glu Val Phe Val Thr Leu Gly Thr Glu Gly Ser
305                 310                 315                 320

Gly Leu Pro Ile Val Pro Gln Val Ser Ser Ile His Asp Met Leu Trp
                325                 330                 335
```

-continued

```
Ala Ala Gly Glu Val Gly Val Gly Ser Glu Gln Glu Gly Ala Lys Val
        340             345             350

Glu Phe Ser Pro Ser Met Ala Gly Phe Leu Asp Trp Gly Phe Ser Ala
        355             360             365

Tyr Ala Ala Ala Gly Lys Val Leu Pro Ala Ser Ser Ala Val Ser Lys
    370             375             380

Thr Ser Gly Val Glu Val Asp Arg Tyr Val Ser Phe Val Trp Leu Thr
385             390             395             400

Gly Asp Gln Tyr Glu Gln Ala Asp Gly Phe Pro Thr Ala Gln Gln Gly
            405             410             415

Trp Thr Gly Ser Leu Leu Leu Pro Arg Glu Leu Lys Val Gln Thr Val
        420             425             430

Glu Asn Val Val Asp Asn Glu Leu Val Arg Glu Glu Gly Val Ser Trp
        435             440             445

Val Val Gly Glu Ser Asp Asn Gln Thr Ala Thr Leu Arg Thr Leu Gly
    450             455             460

Ile Thr Ile Ala Arg Glu Thr Lys Ala Ala Leu Leu Ala Asn Gly Ser
465             470             475             480

Val Thr Ala Glu Glu Asp Arg Thr Leu Gln Thr Ala Ala Val Val Pro
            485             490             495

Phe Ala Gln Ser Pro Ser Ser Lys Phe Phe Val Leu Thr Ala Gln Leu
            500             505             510

Glu Phe Pro Ala Ser Ala Arg Ser Ser Pro Leu Gln Ser Gly Phe Glu
        515             520             525

Ile Leu Ala Ser Glu Leu Glu Arg Thr Ala Ile Tyr Tyr Gln Phe Ser
        530             535             540

Asn Glu Ser Leu Val Val Asp Arg Ser Gln Thr Ser Ala Ala Ala Pro
545             550             555             560

Thr Asn Pro Gly Leu Asp Ser Phe Thr Glu Ser Gly Lys Leu Arg Leu
            565             570             575

Phe Asp Val Ile Glu Asn Gly Gln Glu Gln Val Glu Thr Leu Asp Leu
            580             585             590

Thr Val Val Val Asp Asn Ala Val Val Glu Val Tyr Ala Asn Gly Arg
            595             600             605

Phe Ala Leu Ser Thr Trp Ala Arg Ser Trp Tyr Asp Asn Ser Thr Gln
    610             615             620

Ile Arg Phe Phe His Asn Gly Glu Gly Glu Val Gln Phe Arg Asn Val
625             630             635             640

Ser Val Ser Glu Gly Leu Tyr Asn Ala Trp Pro Glu Arg Lys
            645             650
```

```
<210> SEQ ID NO 2
<211> LENGTH: 1965
<212> TYPE: DNA
<213> ORGANISM: Artificial Sequence
<220> FEATURE:
<223> OTHER INFORMATION: Modified nucleic acid sequence of the gene
      encoding fructosyltransferase

<400> SEQUENCE: 2
atgaaattga ctactactac tttggctttg gctactggtg ctgctgctgc tgaagcttct      60
taccatttgg atactactgc tccacctcca actaatttgt ctactttgcc taacaacact     120
ttgtttcatt tgtggagacc aagagcccat attttgccag ctgaaggtca aattggagat     180
ccatgtgctc actacactga tccatctact ggtttgtttc atgttggttt cttgcacgat     240
```

-continued

```
ggagatggta ttgctggtgc tactactgct aatttggcta cttatactga tacttctgat      300
aacggttctt tcttgattca accaggtggt aaaaacgatc cagttgctgt tttcgatggt      360
gctgttattc ctgttggtgt taacaatact ccaactttgt tgtacacttc tgtttctttc      420
ttgcctattc attggtctat tccatatact agaggttctg aaactcaatc tttggctgtt      480
gctagagatg gtggtagaag attcgataaa ttggatcaag tcctgttat tgctgatcac       540 ccatttgctt tgatgttac tgctttcaga gatcctttg tttttagatc cgctagattg        600
gatgttttgt tgtctttgga tgaagaggtt gctagaaatg agactgctgt tcaacaagct      660
gttgatggtt ggactgaaaa gaacgctcct tggtacgttg ctgtttctgg tggtgttcat      720
ggtgttggtc cagctcaatt tttgtataga caaaacggtg gtaatgcttc tgaattccaa      780
tactgggaat atttgggtga atggtggcaa gaagctacta attcttcttg gggagatgag      840
ggtacttggg ctggtagatg gggtttaac ttcgaaactg gtaacgtttt gtttttgact        900
gaagagggtc acgatccaca aactggagag gttttcgtta ctttgggtac tgaaggttct      960
ggtttgccta ttgttccaca gtttcttct attcacgata tgttgtgggc tgctggtgaa      1020
gttggtgttg ttctgaaca agagggtgct aaggttgaat tttctccttc tatggctggt      1080
ttcttggatt ggggtttctc tgcttacgct gctgctggta aagtttgcc agcttcttct       1140 gctgtttcta aaacttctgg tgttgaggtt gatagatacg tttctttgt ttggttgact      1200 ggagatcaat atgaacaagc tgatggtttc cctactgctc aacaaggttg gactggttct      1260
ttgttgttgc caagagaatt gaaagttcaa actgttgaga cgttgttga taatgaattg       1320 gttagagaag agggtgtttc ttgggttgtt ggagagtctg ataatcaaac tgctactttg      1380
agaactttgg gtattactat tgctagagaa actaaggctg ctttgttggc taacggttct      1440
gttactgctg aagaggatag aactttgcaa actgctgctg ttgttccttt cgctcaatct      1500
ccatcttcta gttttttcgt tttgactgct caattggagt ttcctgcttc tgctagatcc      1560
tctccattgc aatctggttt cgaaattttg gcttctgaat tggagagaac tgctatctac      1620
taccaattct ctaacgagtc tttggttgtt gatagatccc aaacttctgc tgctgctcct      1680
actaacccag gtttggattc ttttactgag tctggtaaat tgagattgtt cgatgttatc      1740
gaaaacggtc aagaacaagt tgagactttg gatttgactg ttgttgttga taacgctgtt      1800
gttgaagttt acgctaatgg tagatttgct ttgtctactt gggctagatc ctggtacgat      1860
aactctactc aaatcagatt tttccacaat ggtgaaggag aggttcaatt cagaaacgtt      1920
tctgtttctg agggtttgta taacgcttgg ccagaaagaa agtga                      1965
```

```
<210> SEQ ID NO 3
<211> LENGTH: 85
<212> TYPE: PRT
<213> ORGANISM: Artificial Sequence
<220> FEATURE:
<223> OTHER INFORMATION: Modified Alpha-factor of S. cerevisiae (FAK)

<400> SEQUENCE: 3

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
```

```
        50              55              60

Phe Ile Asn Thr Thr Ile Ala Ser Ile Ala Ala Lys Glu Glu Gly Val
65                  70              75              80

Ser Leu Glu Lys Arg
                85

<210> SEQ ID NO 4
<211> LENGTH: 89
<212> TYPE: PRT
<213> ORGANISM: Artificial Sequence
<220> FEATURE:
<223> OTHER INFORMATION: Modified Alpha-factor full of S. cerevisiae
      (FAKS)

<400> SEQUENCE: 4

Met Arg Phe Pro Ser Ile Phe Thr Ala Val Leu Phe Ala Ala Ser Ser
1               5               10              15

Ala Leu Ala Ala Pro Val Asn Thr Thr Thr Glu Asp Glu Thr Ala Gln
            20              25              30

Ile Pro Ala Glu Ala Val Ile Gly Tyr Ser Asp Leu Glu Gly Asp Phe
        35              40              45

Asp Val Ala Val Leu Pro Phe Ser Asn Ser Thr Asn Asn Gly Leu Leu
    50              55              60

Phe Ile Asn Thr Thr Ile Ala Ser Ile Ala Ala Lys Glu Glu Gly Val
65                  70              75              80

Ser Leu Glu Lys Arg Glu Ala Glu Ala
                85

<210> SEQ ID NO 5
<211> LENGTH: 23
<212> TYPE: PRT
<213> ORGANISM: Artificial Sequence
<220> FEATURE:
<223> OTHER INFORMATION: Modified Alpha factor_T of S. cerevisiae (AT)

<400> SEQUENCE: 5

Met Arg Phe Pro Ser Ile Phe Thr Ala Val Leu Phe Ala Ala Ser Ser
1               5               10              15

Ala Leu Ala Leu Glu Lys Arg
            20

<210> SEQ ID NO 6
<211> LENGTH: 24
<212> TYPE: PRT
<213> ORGANISM: Artificial Sequence
<220> FEATURE:
<223> OTHER INFORMATION: Modified Alpha-amylase of Aspergillus niger
      (AA)

<400> SEQUENCE: 6

Met Val Ala Trp Trp Ser Leu Phe Leu Tyr Gly Leu Gln Val Ala Ala
1               5               10              15

Pro Ala Leu Ala Leu Glu Lys Arg
            20

<210> SEQ ID NO 7
<211> LENGTH: 22
<212> TYPE: PRT
<213> ORGANISM: Artificial Sequence
<220> FEATURE:
<223> OTHER INFORMATION: Modified Glucoamylase of Aspergillus awamori
      (GA)
```

```
<400> SEQUENCE: 7

Met Ser Phe Arg Ser Leu Leu Ala Leu Ser Gly Leu Val Cys Ser Gly
1               5                   10                  15

Leu Ala Leu Glu Lys Arg
            20

<210> SEQ ID NO 8
<211> LENGTH: 20
<212> TYPE: PRT
<213> ORGANISM: Artificial Sequence
<220> FEATURE:
<223> OTHER INFORMATION: Modified Inulinase of Kluyveromyces maxianus
      (IN)

<400> SEQUENCE: 8

Met Lys Leu Ala Tyr Ser Leu Leu Leu Pro Leu Ala Gly Val Ser Ala
1               5                   10                  15

Leu Glu Lys Arg
            20

<210> SEQ ID NO 9
<211> LENGTH: 23
<212> TYPE: PRT
<213> ORGANISM: Artificial Sequence
<220> FEATURE:
<223> OTHER INFORMATION: Modified Invertase of S. cerevisiae (IV)

<400> SEQUENCE: 9

Met Leu Leu Gln Ala Phe Leu Phe Leu Leu Ala Gly Phe Ala Ala Lys
1               5                   10                  15

Ile Ser Ala Leu Glu Lys Arg
            20

<210> SEQ ID NO 10
<211> LENGTH: 30
<212> TYPE: PRT
<213> ORGANISM: Artificial Sequence
<220> FEATURE:
<223> OTHER INFORMATION: Modified Killer protein of S. cerevisiae (KP)

<400> SEQUENCE: 10

Met Thr Lys Pro Thr Gln Val Leu Val Arg Ser Val Ser Ile Leu Phe
1               5                   10                  15

Phe Ile Thr Leu Leu His Leu Val Val Ala Leu Glu Lys Arg
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Modified Lysozyme of Gallus gallus (LZ)

<400> SEQUENCE: 11

Met Leu Gly Lys Asn Asp Pro Met Cys Leu Val Leu Val Leu Leu Gly
1               5                   10                  15

Leu Thr Ala Leu Leu Gly Ile Cys Gln Gly Leu Glu Lys Arg
            20                  25                  30

<210> SEQ ID NO 12
<211> LENGTH: 22
<212> TYPE: PRT
<213> ORGANISM: Artificial Sequence
<220> FEATURE:
```

<223> OTHER INFORMATION: Modified Serum albumin of Homo sapiens (SA)

<400> SEQUENCE: 12

Met Lys Trp Val Thr Phe Ile Ser Leu Leu Phe Leu Phe Ser Ser Ala
1               5                   10                  15

Tyr Ser Leu Glu Lys Arg
            20

<210> SEQ ID NO 13
<211> LENGTH: 2220
<212> TYPE: DNA
<213> ORGANISM: Artificial Sequence
<220> FEATURE:
<223> OTHER INFORMATION: Alpha-factor (FAK) of S. cerevisiae fused to
      modified nucleic acid of fructosyltransferase gene

<400> SEQUENCE: 13
atgagatttc cttcaatttt tactgctgtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaagggggta     240 tctctcgaga agagaatgaa attgactact actactttgg cctttggctac tggtgctgct     300 gctgctgaag cttcttacca tttggatact actgctccac ctccaactaa tttgtctact     360
ttgcctaaca acactttgtt tcatttgtgg agaccaagag cccatatttt gccagctgaa     420
ggtcaaattg gagatccatg tgctcactac actgatccat ctactggttt gtttcatgtt     480
ggtttcttgc acgatggaga tggtattgct ggtgctacta ctgctaattt ggctacttat     540
actgatactt ctgataacgg ttctttcttg attcaaccag gtggtaaaaa cgatccagtt     600
gctgttttcg atggtgctgt tattcctgtt ggtgttaaca atactccaac tttgttgtac     660
acttctgttt ctttcttgcc tattcattgg tctattccat atactagagg ttctgaaact     720
caatctttgg ctgttgctag agatggtggt agaagattcg ataaattgga tcaaggtcct     780
gttattgctg atcacccatt tgctgttgat gttactgctt tcagagatcc ttttgttttt     840
agatccgcta gattggatgt tttgttgtct ttggatgaag aggttgctag aaatgagact     900
gctgttcaac aagctgttga tggttggact gaaaagaacg ctccttggta cgttgctgtt     960
tctggtggtg ttcatggtgt tggtccagct caatttttgt atagacaaaa cggtggtaat    1020
gcttctgaat ccaatactg ggaatatttg ggtgaatggt ggcaagaagc tactaattct    1080
tcttggggag atgagggtac ttgggctggt agatgggggt ttaacttcga aactggtaac    1140
gttttgtttt tgactgaaga gggtcacgat ccacaaactg agaggttttt cgttactttg    1200
ggtactgaag ttctggtttt gcctattgtt ccacaagttt cttctattca cgatatgttg    1260
tgggctgctg gtgaagttgg tgttggttct gaacaagagg gtgctaaggt tgaatttttct    1320 ccttctatgg ctggtttctt ggattggggt ttctctgctt acgctgctgc tggtaaagtt    1380
ttgccagctt cttctgctgt ttctaaaact tctggtgttg aggttgatag atacgtttct    1440
tttgtttggt tgactggaga tcaatatgaa caagctgatg gtttccctac tgctcaacaa    1500
ggttggactg ttctttgtt gttgccaaga gaattgaaag ttcaaactgt tgagaacgtt    1560
gttgataatg aattggttag agaagagggt gtttcttggg ttgttggaga gtctgataat    1620
caaactgcta ctttgagaac tttgggtatt actattgcta gagaaactaa ggctgctttg    1680
ttggctaacg ttctgttac tgctgaagag gatagaactt gcaaactgc tgctgttgtt    1740

-continued

```
cctttcgctc aatctccatc ttctaagttt ttcgttttga ctgctcaatt ggagtttcct    1800
gcttctgcta gatcctctcc attgcaatct ggtttcgaaa ttttggcttc tgaattggag    1860
agaactgcta tctactacca attctctaac gagtctttgg ttgttgatag atcccaaact    1920
tctgctgctg ctcctactaa cccaggtttg gattctttta ctgagtctgg taaattgaga    1980
ttgttcgatg ttatcgaaaa cggtcaagaa caagttgaga ctttggattt gactgttgtt    2040
gttgataacg ctgttgttga agtttacgct aatggtagat ttgctttgtc tacttgggct    2100
agatcctggt acgataactc tactcaaatc agattttttcc acaatggtga aggagaggtt    2160
caattcagaa acgtttctgt ttctgagggt ttgtataacg cttggccaga aagaaagtga    2220
```

<210> SEQ ID NO 14
<211> LENGTH: 2232
<212> TYPE: DNA
<213> ORGANISM: Artificial Sequence
<220> FEATURE:
<223> OTHER INFORMATION: Alpha-factor full (FAKS) of S. cerevisiae fused
      to modified nucleic acid of fructosyltransferase gene

<400> SEQUENCE: 14

```
atgagatttc cttcaatttt tactgctgtt ttattcgcag catcctccgc attagctgct      60
ccagtcaaca ctacaacaga agatgaaacg gcacaaattc cggctgaagc tgtcatcggt     120
tactcagatt tagaaggggga tttcgatgtt gctgttttgc cattttccaa cagcacaaat     180
aacgggttat tgtttataaa tactactatt gccagcattg ctgctaaaga agaaggggta     240
tctctcgaga agagagaggc tgaagctatg aaattgacta ctactacttt ggctttggct     300
actggtgctg ctgctgctga agcttcttac catttggata ctactgctcc acctccaact     360
aatttgtcta ctttgcctaa caacactttg tttcatttgt ggagaccaag agcccatatt     420
ttgccagctg aaggtcaaat tggagatcca tgtgctcact acactgatcc atctactggt     480
ttgtttcatg ttggtttctt gcacgatgga gatggtattg ctggtgctac tactgctaat     540
ttggctactt atactgatac ttctgataac ggttctttct tgattcaacc aggtggtaaa     600
aacgatccag ttgctgtttt cgatggtgct gttattcctg ttggtgttaa caatactcca     660
actttgttgt acacttctgt ttctttcttg cctattcatt ggtctattcc atatactaga     720
ggttctgaaa ctcaatcttt ggctgttgct agagatggtg gtagaagatt cgataaattg     780
gatcaaggtc ctgttattgc tgatcaccca tttgctgttg atgttactgc tttcagagat     840
ccttttgttt ttagatccgc tagattggat gttttgttgt ctttggatga agaggttgct     900
agaaatgaga ctgctgttca acaagctgtt gatggttgga ctgaaaagaa cgctccttgg     960
tacgttgctg tttctggtgg tgttcatggt gttggtccag ctcaattttt gtatagacaa    1020
aacggtggta atgcttctga attccaatac tgggaatatt tgggtgaatg gtggcaagaa    1080
gctactaatt cttcttgggg agatgagggt acttgggctg gtagatgggg ttttaacttc    1140
gaaactggta acgttttgtt tttgactgaa gaggtcacg atccacaaac tggagaggtt     1200
ttcgttactt tgggtactga aggttctggt ttgcctattg ttccacaagt ttcttctatt    1260
cacgatatgt tgtgggctgc tggtgaagtt ggtgttggtt ctgaacaaga gggtgctaag    1320
gttgaatttt ctccttctat ggctggtttc ttggattggg gtttctctgc ttacgctgct    1380
gctggtaaag ttttgccagc ttcttctgct gtttctaaaa cttctggtgt tgaggttgat    1440
agatacgttt cttttgtttg gttgactgga gatcaatatg aacaagctga tggtttccct    1500
actgctcaac aaggttggac tggttctttg ttgttgccaa gagaattgaa agttcaaact    1560
```

```
gttgagaacg ttgttgataa tgaattggtt agagaagagg gtgtttcttg ggttgttgga      1620
gagtctgata atcaaactgc tactttgaga actttgggta ttactattgc tagagaaact      1680
aaggctgctt tgttggctaa cggttctgtt actgctgaag aggatagaac tttgcaaact      1740
gctgctgttg ttcctttcgc tcaatctcca tcttctaagt ttttcgtttt gactgctcaa      1800
ttggagtttc ctgcttctgc tagatcctct ccattgcaat ctggtttcga aattttggct      1860
tctgaattgg agagaactgc tatctactac caattctcta acgagtcttt ggttgttgat      1920
agatcccaaa cttctgctgc tgctcctact aacccaggtt tggattcttt tactgagtct      1980
ggtaaattga gattgttcga tgttatcgaa aacggtcaag aacaagttga gactttggat      2040
ttgactgttg ttgttgataa cgctgttgtt gaagtttacg ctaatggtag atttgctttg      2100
tctacttggg ctagatcctg gtacgataac tctactcaaa tcagattttt ccacaatggt      2160
gaaggagagg ttcaattcag aaacgtttct gtttctgagg gtttgtataa cgcttggcca      2220
gaaagaaagt ga                                                          2232
```

```
<210> SEQ ID NO 15
<211> LENGTH: 2034
<212> TYPE: DNA
<213> ORGANISM: Artificial Sequence
<220> FEATURE:
<223> OTHER INFORMATION: Alpha-factor_T (AT) of S. cerevisiae fused to
      modified nucleic acid of fructosyltransferase gene

<400> SEQUENCE: 15
```

```
atgagatttc cttcaatttt tactgctgtt ttattcgcag catcctccgc attagctctc        60
gagaagagaa tgaaattgac tactactact ttggctttgg ctactggtgc tgctgctgct       120
gaagcttctt accatttgga tactactgct ccacctccaa ctaatttgtc tactttgcct       180
aacaacactt tgtttcattt gtggagacca agagcccata ttttgccagc tgaaggtcaa       240
attggagatc catgtgctca ctacactgat ccatctactg gtttgtttca tgttggtttc       300
ttgcacgatg gagatggtat tgctggtgct actactgcta atttggctac ttatactgat       360
acttctgata acggttcttt cttgattcaa ccaggtggta aaaacgatcc agttgctgtt       420
ttcgatggtg ctgttattcc tgttggtgtt aacaatactc caactttgtt gtacacttct       480
gtttctttct tgcctattca ttggtctatt ccatatacta gaggttctga aactcaatct       540
ttggctgttg ctagagatgg tggtagaaga ttcgataaat tggatcaagg tcctgttatt       600
gctgatcacc catttgctgt tgatgttact gctttcagag atccttttgt ttttagatcc       660
gctagattgg atgttttgtt gtctttggat gaagaggttg ctagaaatga gactgctgtt       720
caacaagctg ttgatggttg gactgaaaag aacgctcctt ggtacgttgc tgtttctggt       780
ggtgttcatg tgttggtcc agctcaattt ttgtatagac aaaacggtgg taatgcttct       840
gaattccaat actgggaata tttgggtgaa tggtggcaag aagctactaa ttcttcttgg       900
ggagatgagg taacttgggc tggtagatgg ggttttaact tcgaaactgg taacgttttg       960
tttttgactg aagagggtca cgatccacaa actggagagg ttttcgttac tttgggtact      1020
gaaggttctg gtttgcctat tgttccacaa gtttcttcta ttcacgatat gttgtgggct      1080
gctggtgaag ttggtgttgg ttctgaacaa gagggtgcta aggttgaatt ttctccttct      1140
atggctggtt tcttggattg gggtttctct gcttacgctg ctgctggtaa agttttgcca      1200
gcttcttctg ctgtttctaa aacttctggt gttgaggttg atagatacgt ttcttttgtt      1260
tggttgactg gagatcaata tgaacaagct gatggtttcc ctactgctca acaaggttgg      1320
```
actggttctt tgttgttgcc aagagaattg aaagttcaaa ctgttgagaa cgttgttgat    1380
aatgaattgg ttagagaaga gggtgtttct tgggttgttg gagagtctga taatcaaact    1440
gctactttga gaactttggg tattactatt gctagagaaa ctaaggctgc tttgttggct    1500
aacggttctg ttactgctga gaggatagaa actttgcaaa ctgctgctgt tgttcctttc    1560
gctcaatctc catcttctaa gttttttcgtt ttgactgctc aattggagtt tcctgcttct    1620
gctagatcct ctccattgca atctggtttc gaaattttgg cttctgaatt ggagagaact    1680
gctatctact accaattctc taacgagtct ttggttgttg atagatccca aacttctgct    1740
gctgctccta ctaacccagg tttggattct tttactgagt ctggtaaatt gagattgttc    1800
gatgttatcg aaaacggtca agaacaagtt gagactttgg atttgactgt tgttgttgat    1860
aacgctgttg ttgaagttta cgctaatggt agatttgctt tgtctacttg ggctagatcc    1920
tggtacgata actctactca aatcagattt ttccacaatg gtgaaggaga ggttcaattc    1980
agaaacgttt ctgtttctga gggtttgtat aacgcttggc cagaaagaaa gtga         2034

<210> SEQ ID NO 16
<211> LENGTH: 2037
<212> TYPE: DNA
<213> ORGANISM: Artificial Sequence
<220> FEATURE:
<223> OTHER INFORMATION: Alpha-amylase (AA) of Aspergillus niger fused
      to modified nucleic acid of fructosyltransferase gene

<400> SEQUENCE: 16
atggttgctt ggtggagtct tttcctatac ggtctacagg tggcagctcc agcccttgcc      60
ctcgagaaga gaatgaaatt gactactact actttggctt tggctactgg tgctgctgct     120
gctgaagctt cttaccattt ggatactact gctccacctc caactaattt gtctactttg     180
cctaacaaca ctttgtttca tttgtggaga ccaagagccc atattttgcc agctgaaggt     240
caaattggag atccatgtgc tcactacact gatccatcta ctggtttgtt tcatgttggt     300
ttcttgcacg atggagatgg tattgctggt gctactactc taatttggc tacttatact     360 gatacttctg ataacggttc tttcttgatt caaccaggtg gtaaaaacga tccagttgct     420
gttttcgatg gtgctgttat tcctgttggt gttaacaata ctccaacttt gttgtacact     480
tctgtttctt tcttgcctat tcattggtct attccatata ctagaggttc tgaaactcaa     540
tctttggctg ttgctagaga tggtggtaga agattcgata aattggatca aggtcctgtt     600
attgctgatc acccatttgc tgttgatgtt actgctttca gagatccttt tgtttttaga     660
tccgctagat tggatgtttt tgttgtctttg gatgaagagg ttgctagaaa tgagactgct     720
gttcaacaag ctgttgatgg ttggactgaa aagaacgctc cttggtacgt tgctgtttct     780
ggtggtgttc atggtgttgg tccagctcaa tttttgtata gacaaaacgg tggtaatgct     840
tctgaattcc aatactggga atatttgggt gaatggtggc aagaagctac taattcttct     900
tggggagatg agggtacttg ggctggtaga tggggtttta acttcgaaac tggtaacgtt     960
ttgtttttga ctgaagaggg tcacgatcca caaactggag aggttttcgt tactttgggt    1020
actgaaggtt ctggtttgcc tattgttcca caagtttctt ctattcacga tatgttgtgg    1080
gctgctggta agttggtgt tggttctgaa caagagggtc taaggttga attttctcct    1140 tctatggctg gtttcttgga ttggggtttc tctgcttacg ctgctgctgg taaagttttg    1200
ccagcttctt ctgctgtttc taaaacttct ggtgttgagg ttgatagata cgtttctttt    1260
gtttggttga ctggagatca atatgaacaa gctgatggtt ccctactgc tcaacaaggt    1320

```
tggactggtt ctttgttgtt gccaagagaa ttgaaagttc aaactgttga gaacgttgtt    1380
gataatgaat tggttagaga agagggtgtt tcttgggttg ttggagagtc tgataatcaa    1440
actgctactt tgagaacttt gggtattact attgctagag aaactaaggc tgctttgttg    1500
gctaacggtt ctgttactgc tgaagaggat agaactttgc aaactgctgc tgttgttcct    1560
ttcgctcaat ctccatcttc taagttttte gttttgactg ctcaattgga gtttcctgct    1620
tctgctagat cctctccatt gcaatctggt ttcgaaattt tggcttctga attggagaga    1680
actgctatct actaccaatt ctctaacgag tctttggttg ttgatagatc ccaaacttct    1740
gctgctgctc ctactaaccc aggtttggat tcttttactg agtctggtaa attgagattg    1800
ttcgatgtta tcgaaaacgg tcaagaacaa gttgagactt ggatttgac tgttgttgtt    1860 gataacgctg ttgttgaagt ttacgctaat ggtagatttg ctttgtctac ttgggctaga    1920
tcctggtacg ataactctac tcaaatcaga ttttttccaca atggtgaagg agaggttcaa    1980
ttcagaaacg tttctgtttc tgagggtttg tataacgctt ggccagaaag aaagtga      2037

<210> SEQ ID NO 17
<211> LENGTH: 2031
<212> TYPE: DNA
<213> ORGANISM: Artificial Sequence
<220> FEATURE:
<223> OTHER INFORMATION: Glucoamylase (GA) of Aspergillus awamori fused
      to modified nucleic acid of fructosyltransferase gene

<400> SEQUENCE: 17
atgtctttcc gatctctttt agccctatct ggacttgttt gttcaggttt ggctctcgag      60
aagagaatga aattgactac tactactttg gctttggcta ctggtgctgc tgctgctgaa     120
gcttcttacc atttggatac tactgctcca cctccaacta atttgtctac tttgcctaac     180
aacactttgt ttcatttgtg gagaccaaga gcccatattt gccagctga aggtcaaatt       240 ggagatccat gtgctcacta cactgatcca tctactggtt tgtttcatgt tggtttcttg     300
cacgatggag atggtattgc tggtgctact actgctaatt tggctactta tactgatact     360
tctgataacg gttctttctt gattcaacca ggtggtaaaa acgatccagt tgctgtttc      420 gatggtgctg ttattcctgt tggtgttaac aatactccaa ctttgttgta cacttctgtt     480 tcttttcttgc ctattcattg gtctattcca tatactagag ttctgaaac tcaatctttg     540 gctgttgcta gagatggtgg tagaagattc gataaattgg atcaaggtcc tgttattgct     600
gatcacccat ttgctgttga gttactgct ttcagagatc cttttgtttt tagatccgct      660
agattggatg ttttgttgtc tttggatgaa gaggttgcta gaaatgagac tgctgttcaa     720
caagctgttg atggttggac tgaaaagaac gctccttggt acgttgctgt ttctggtggt     780
gttcatggtt ttggtccagc tcaattttttg tatagacaaa acggtggtaa tgcttctgaa     840
ttccaatact gggaatattt gggtgaatgg tggcaagaag ctactaattc ttcttgggga     900
gatgagggta cttgggctgg tagatggggt tttaacttcg aaactggtaa cgttttgttt      960
ttgactgaag agggtcacga tccacaaact ggagaggttt cgttactttt gggtactgaa     1020
ggttctggtt tgcctattgt tccacaagtt tcttctattc acgatatgtt gtgggctgct    1080
ggtgaagttg gtgttggttc tgaacaagag ggtgctaagg ttgaattttc tccttctatg    1140
gctggtttct tggattgggg tttctctgct tacgctgctg ctggtaaagt tttgccagct    1200
tcttctgctg tttctaaaac ttctggtgtt gaggttgata gatacgtttc ttttgtttgg    1260
ttgactggag atcaatatga acaagctgat ggtttcccta ctgctcaaca aggttggact    1320
```

-continued

```
ggttctttgt tgttgccaag agaattgaaa gttcaaactg ttgagaacgt tgttgataat   1380
gaattggtta gagaagaggg tgtttcttgg gttgttggag agtctgataa tcaaactgct   1440
actttgagaa ctttgggtat tactattgct agagaaacta aggctgcttt gttggctaac   1500
ggttctgtta ctgctgaaga ggatagaact ttgcaaactg ctgctgttgt tcctttcgct   1560
caatctccat cttctaagtt tttcgttttg actgctcaat ggagtttcc tgcttctgct   1620 agatcctctc cattgcaatc tggtttcgaa attttggctt ctgaattgga gagaactgct   1680
atctactacc aattctctaa cgagtctttg gttgttgata gatcccaaac ttctgctgct   1740
gctcctacta acccaggttt ggattctttt actgagtctg gtaaattgag attgttcgat   1800
gttatcgaaa acggtcaaga acaagttgag actttggatt tgactgttgt tgttgataac   1860
gctgttgttg aagtttacgc taatggtaga tttgctttgt ctacttgggc tagatcctgg   1920
tacgataact ctactcaaat cagatttttc cacaatggtg aaggagaggt tcaattcaga   1980
aacgtttctg tttctgaggg tttgtataac gcttggccag aaagaaagtg a            2031
```

<210> SEQ ID NO 18
<211> LENGTH: 2025
<212> TYPE: DNA
<213> ORGANISM: Artificial Sequence
<220> FEATURE:
<223> OTHER INFORMATION: Inulinase (IN) of Kluyveromyces maxianus fused
     to modified nucleic acid of fructosyltransferase gene

<400> SEQUENCE: 18

```
atgaagttgg cttattctct tcttcttcct ctggccggag tgtctgccct cgagaagaga    60
atgaaattga ctactactac tttggctttg gctactggtg ctgctgctgc tgaagcttct   120
taccatttgg atactactgc tccacctcca actaatttgt ctacttttgcc taacaacact   180 ttgtttcatt tgtggagacc aagagcccat attttgccag ctgaaggtca aattggagat   240
ccatgtgctc actacactga tccatctact ggtttgtttc atgttggttt cttgcacgat   300
ggagatggta ttgctggtgc tactactgct aatttggcta cttatactga tacttctgat   360
aacggttctt tcttgattca accaggtggt aaaaacgatc cagttgctgt tttcgatggt   420
gctgttattc ctgttggtgt taacaatact ccaactttgt tgtacacttc tgtttctttc   480
ttgcctattc attggtctat tccatatact agaggttctg aaactcaatc tttggctgtt   540
gctagagatg tggtagaag attcgataaa ttggatcaag tcctgttat tgctgatcac   600 ccatttgctg ttgatgttac tgctttcaga gatccttttg tttttagatc cgctagattg   660
gatgttttgt tgtctttgga tgaagaggtt gctagaaatg agactgctgt tcaacaagct   720
gttgatggtt ggactgaaaa gaacgctcct tggtacgttg ctgtttctgg tggtgttcat   780
ggtgttggtc cagctcaatt tttgtataga caaaacggtg gtaatgcttc tgaattccaa   840
tactgggaat atttgggtga atggtggcaa gaagctacta attcttcttg gggagatgag   900
ggtacttggg ctggtagatg gggtttaac ttcgaaactg gtaacgtttt gttttttgact   960 gaagagggtc acgatccaca aactggagag gttttcgtta ctttgggtac tgaaggttct   1020
ggtttgccta ttgttccaca gtttttcttct attcacgata tgttgtgggc tgctggtgaa   1080
gttggtgttg ttctgaaca agagggtgct aaggttgaat tttctccttc tatggctggt   1140
ttcttggatt ggggtttctc tgcttacgct gctgctggta agttttttgcc agcttcttct   1200 gctgtttcta aaacttctgg tgttgaggtt gatagatacg tttctttttgt ttggttgact   1260 ggagatcaat atgaacaagc tgatggtttc cctactgctc aacaaggttg gactggttct   1320
```

```
ttgttgttgc caagagaatt gaaagttcaa actgttgaga acgttgttga taatgaattg    1380
gttagagaag aggqtqtttc ttgggttgtt ggagagtctg ataatcaaac tgctactttg    1440
agaactttgg gtattactat tgctagagaa actaaggctg ctttgttggc taacggttct    1500
gttactgctg aagaggatag aactttgcaa actgctgctg ttgttccttt cgctcaatct    1560
ccatcttcta agtttttcgt tttgactgct caattggagt ttcctgcttc tgctagatcc    1620
tctccattgc aatctggttt cgaaattttg gcttctgaat tggagagaac tgctatctac    1680
taccaattct ctaacgagtc tttggttgtt gatagatccc aaacttctgc tgctgctcct    1740
actaacccag gtttggattc ttttactgag tctggtaaat tgagattgtt cgatgttatc    1800
gaaaacggtc aagaacaagt tgagactttg gatttgactg ttgttgttga taacgctgtt    1860
gttgaagttt acgctaatgg tagatttgct ttgtctactt gggctagatc ctggtacgat    1920
aactctactc aaatcagatt tttccacaat ggtgaaggag aggttcaatt cagaaacgtt    1980
tctgtttctg agggtttgta taacgcttgg ccagaaagaa agtga                    2025
```

<210> SEQ ID NO 19
<211> LENGTH: 2034
<212> TYPE: DNA
<213> ORGANISM: Artificial Sequence
<220> FEATURE:
<223> OTHER INFORMATION: Invertase (IV) of S.cerevisiae fused to
      modified nucleic acid of fructosyltransferase gene

<400> SEQUENCE: 19

```
atgctttttgc aggctttcct gttcttgctg gccggattcg ctgctaaaat ttccgctctc     60
gagaagagaa tgaaattgac tactactact ttggctttgg ctactggtgc tgctgctgct    120
gaagcttctt accatttgga tactactgct ccacctccaa ctaatttgtc tactttgcct    180
aacaacactt tgtttcattt gtggagacca agagcccata ttttgccagc tgaaggtcaa    240
attggagatc catgtgctca ctacactgat ccatctactg gtttgtttca tgttggtttc    300
ttgcacgatg gagatggtat tgctggtgct actactgcta atttggctac ttatactgat    360
acttctgata acggttcttt cttgattcaa ccaggtggta aaaacgatcc agttgctgtt    420
ttcgatggtg ctgttattcc tgttggtgtt aacaatactc aactttgtt gtacacttct    480 gtttctttct tgcctattca ttggtctatt ccatatacta gaggttctga aactcaatct    540
ttggctgttg ctagagatgg tggtagaaga ttcgataaat tggatcaagg tcctgttatt    600
gctgatcacc catttgctgt tgatgttact gctttcagag atccttttgt ttttagatcc    660
gctagattgg atgtttttgtt gtctttggat aagaggttc ctagaaatga gactgctgtt    720
caacaagctg ttgatggttg gactgaaaag aacgctcctt ggtacgttgc tgtttctggt    780
ggtgttcatg tgttggtcc agctcaattt ttgtatagac aaaacggtgg taatgcttct    840
gaattccaat actgggaata tttgggtgaa tggtggcaag aagctactaa ttcttcttgg    900
ggagatgagg gtacttgggc tggtagatgg ggttttaact tcgaaactgg taacgttttg    960
tttttgactg aagagggtca cgatccacaa actggagagg ttttcgttac tttgggtact    1020
gaaggttctg gtttgcctat tgttccacaa gtttcttcta ttcacgatat gttgtgggct    1080
gctggtgaag ttggtgttgg ttctgaacaa gagggtgcta aggttgaatt ttctccttct    1140
atggctggtt tcttggattg gggtttctct gcttacgctg ctgctggtaa agttttgcca    1200
gcttcttctg ctgtttctaa aacttctggt gttgaggtta tagatacgt ttcttttgtt    1260 tggttgactg gagatcaata tgaacaagct gatggtttcc ctactgctca acaaggttgg    1320
```

-continued

```
actggttctt tgttgttgcc aagagaattg aaagttcaaa ctgttgagaa cgttgttgat    1380
aatgaattgg ttagagaaga gggtgtttct tgggttgttg gagagtctga taatcaaact    1440
gctactttga gaactttggg tattactatt gctagagaaa ctaaggctgc tttgttggct    1500
aacggttctg ttactgctga agaggataga actttgcaaa ctgctgctgt tgttcctttc    1560
gctcaatctc catcttctaa gttttttcgtt ttgactgctc aattggagtt tcctgcttct    1620
gctagatcct ctccattgca atctggtttc gaaattttgg cttctgaatt ggagagaact    1680
gctatctact accaattctc taacgagtct ttggttgttg atagatccca aacttctgct    1740
gctgctccta ctaacccagg tttggattct tttactgagt ctggtaaatt gagattgttc    1800
gatgttatcg aaaacggtca agaacaagtt gagactttgg atttgactgt tgttgttgat    1860
aacgctgttg ttgaagtttta cgctaatggt agatttgctt tgtctacttg ggctagatcc    1920
tggtacgata actctactca aatcagattt ttccacaatg gtgaaggaga ggttcaattc    1980
agaaacgttt ctgtttctga gggtttgtat aacgcttggc cagaaagaaa gtga          2034
```

```
<210> SEQ ID NO 20
<211> LENGTH: 2055
<212> TYPE: DNA
<213> ORGANISM: Artificial Sequence
<220> FEATURE:
<223> OTHER INFORMATION: Killer protein (KP) of S.cerevisiae fused to
      modified nucleic acid of fructosyltransferase gene

<400> SEQUENCE: 20
```

```
atgaccaaac caactcaagt tttggtgagg tctgtgtcaa tcctgttctt cattactttat    60 ctgcaccttg tagtcgcact cgagaagaga atgaaattga ctactactac tttggctttg    120
gctactggtg ctgctgctgc tgaagcttct taccatttgg atactactgc tccacctcca    180
actaatttgt ctactttgcc taacaacact ttgtttcatt tgtggagacc aagagcccat    240
attttgccag ctgaaggtca aattggagat ccatgtgctc actacactga tccatctact    300
ggtttgtttc atgttggttt cttgcacgat ggagatggta ttgctggtgc tactactgct    360
aatttggcta cttatactga tacttctgat aacggttctt tcttgattca accaggtggt    420
aaaaacgatc cagttgctgt tttcgatggt gctgttattc ctgttggtgt taacaatact    480
ccaactttgt tgtacacttc tgtttctttc ttgcctattc attggtctat tccatatact    540
agaggttctg aaactcaatc tttggctgtt gctagagatg gtggtagaag attcgataaa    600
ttggatcaag gtcctgttat tgctgatcac ccatttgctg ttgatgttac tgctttcaga    660
gatccttttg tttttagatc cgctagattg gatgttttgt tgtctttgga tgaagaggtt    720
gctagaaatg agactgctgt tcaacaagct gttgatggtt ggactgaaaa gaacgctcct    780
tggtacgttg ctgtttctgg tggtgttcat ggtgttggtc cagctcaatt tttgtataga    840
caaaacggtg gtaatgcttc tgaattccaa tactgggaat atttgggtga atggtggcaa    900
gaagctacta attcttcttg gggagatgag ggtacttggg ctggtagatg gggtttttaac    960 ttcgaaactg gtaacgtttt gttttttgact gaagagggtc acgatccaca aactggagag    1020
gttttcgtta ctttgggtac tgaaggttct ggtttgccta ttgttccaca gtttcttct    1080 attcacgata tgttgtgggc tgctggtgaa gttggtgttg ttctgaaca agagggtgct    1140 aaggttgaat tttctccttc tatggctggt ttcttggatt ggggtttctc tgcttacgct    1200
gctgctggta agttttgcc agcttcttct gctgtttcta aaacttctgg tgttgaggtt    1260
gatagatacg tttcttttgt ttggttgact ggagatcaat atgaacaagc tgatggtttc    1320
```

```
cctactgctc aacaaggttg gactggttct ttgttgttgc caagagaatt gaaagttcaa    1380
actgttgaga acgttgttga taatgaattg gttagagaag agggtgtttc ttgggttgtt    1440
ggagagtctg ataatcaaac tgctactttg agaactttgg gtattactat tgctagagaa    1500
actaaggctc ctttgttggc taacggttct gttactgctg aagaggatag aactttgcaa    1560
actgctgctg ttgttccttt cgctcaatct ccatcttcta agttttttcgt tttgactgct    1620 caattggagt ttcctgcttc tgctagatcc tctccattgc aatctggttt cgaaattttg    1680
gcttctgaat ggagagaac tgctatctac taccaattct ctaacgagtc tttggttgtt    1740
gatagatccc aaacttctgc tgctgctcct actaacccag gtttggattc ttttactgag    1800
tctggtaaat tgagattgtt cgatgttatc gaaaacggtc aagaacaagt tgagactttg    1860
gatttgactg ttgttgttga taacgctgtt gttgaagttt acgctaatgg tagatttgct    1920
ttgtctactt gggctagatc ctggtacgat aactctactc aaatcagatt tttccacaat    1980
ggtgaaggag aggttcaatt cagaaacgtt tctgtttctg agggtttgta taacgcttgg    2040
ccagaaagaa agtga                                                    2055
```

```
<210> SEQ ID NO 21
<211> LENGTH: 2055
<212> TYPE: DNA
<213> ORGANISM: Artificial Sequence
<220> FEATURE:
<223> OTHER INFORMATION: Lysozyme (LZ) of Gallus gallus fused to
      modified nucleic acid of fructosyltransferase gene

<400> SEQUENCE: 21
```

```
atgctaggca aaaatgaccc tatgtgtttg gttctggttt tgcttggttt aaccgcttta      60
cttggtatct gtcaaggtct cgagaagaga atgaaattga ctactactac tttggctttg     120
gctactggtg ctgctgctgc tgaagcttct taccatttgg atactactgc tccacctcca     180
actaatttgt ctactttgcc taacaacact ttgtttcatt tgtggagacc aagagcccat     240
attttgccag ctgaaggtca aattggagat ccatgtgctc actacactga tccatctact     300
ggtttgtttc atgttggttt cttgcacgat ggagatggta ttgctggtgc tactactgct     360
aatttggcta cttatactga tacttctgat aacggttctt cttgattca accaggtggt     420 aaaaacgatc cagttgctgt tttcgatggt gctgttattc ctgttggtgt taacaatact     480
ccaactttgt tgtacacttc tgtttctttc ttgcctattc attggtctat tccatatact     540
agaggttctg aaactcaatc tttggctgtt gctagagatg gtggtagaag attcgataaa     600
ttggatcaag gtcctgttat tgctgatcac ccatttgctg ttgatgttac tgctttcaga     660 gatcctttg tttttagatc cgctagattg gatgtttttgt tgtctttgga tgaagaggtt     720
gctagaaatg agactgctgt tcaacaagct gttgatggtt ggactgaaaa gaacgctcct     780
tggtacgttg ctgtttctgg tggtgttcat ggtgttggtc agctcaatt tttgtataga     840 caaaacggtg gtaatgcttc tgaattccaa tactgggaat atttgggtga atggtggcaa     900
gaagctacta attcttcttg gggagatgag ggtacttggg ctggtagatg gggttttaac     960
ttcgaaactg gtaacgtttt gttttttgact gaagagggtc acgatccaca aactggagag    1020
gttttcgtta ctttgggtac tgaaggttct ggtttgccta ttgttccaca gtttcttct     1080 attcacgata tgttgtgggc tgctggtgaa gttggtgttg ttctgaaca gagagggtgct     1140 aaggttgaat ttctcctcc tatggctggt ttccttggatt ggggtttctc tgcttacgct    1200
gctgctggta agttttgcc agcttcttct gctgtttcta aaacttctgg tgttgaggtt     1260
```

-continued

```
gatagatacg tttcttttgt ttggttgact ggagatcaat atgaacaagc tgatggtttc      1320
cctactgctc aacaaggttg gactggttct ttgttgttgc caagagaatt gaaagttcaa      1380
actgttgaga acgttgttga taatgaattg gttagagaag agggtgtttc ttgggttgtt      1440
ggagagtctg ataatcaaac tgctactttg agaactttgg gtattactat tgctagagaa      1500
actaaggctg ctttgttggc taacggttct gttactgctg aagaggatag aactttgcaa      1560
actgctgctg ttgttccttt cgctcaatct ccatcttcta agttttttcgt tttgactgct      1620 caattggagt ttcctgcttc tgctagatcc tctccattgc aatctggttt cgaaattttg      1680
gcttctgaat ggagagaac tgctatctac taccaattct ctaacgagtc tttggttgtt      1740
gatagatccc aaacttctgc tgctgctcct actaacccag gtttggattc ttttactgag      1800
tctggtaaat tgagattgtt cgatgttatc gaaaacggtc aagaacaagt tgagactttg      1860
gatttgactg ttgttgttga taacgctgtt gttgaagttt acgctaatgg tagatttgct      1920
ttgtctactt gggctagatc ctggtacgat aactctactc aaatcagatt tttccacaat      1980
ggtgaaggag aggttcaatt cagaaacgtt tctgtttctg agggtttgta taacgcttgg      2040
ccagaaagaa agtga                                                        2055
```

```
<210> SEQ ID NO 22
<211> LENGTH: 2031
<212> TYPE: DNA
<213> ORGANISM: Artificial Sequence
<220> FEATURE:
<223> OTHER INFORMATION: Serum albumin (SA) of Homo sapiens fused to
      modified nucleic acid of fructosyltransferase gene

<400> SEQUENCE: 22
```

```
atgaagtggg taacatttat ttccctactg tttctttttt cttcagctta ctctctcgag        60
aagagaatga aattgactac tactactttg gctttggcta ctggtgctgc tgctgctgaa       120
gcttcttacc atttggatac tactgctcca cctccaacta atttgtctac tttgcctaac       180
aacactttgt ttcatttgtg gagaccaaga gcccatattt gccagctga aggtcaaatt        240 ggagatccat gtgctcacta cactgatcca tctactggtt gtttcatgt ggtttcttg         300 cacgatggag atggtattgc tggtgctact actgctaatt tggctactta tactgatact       360
tctgataacg ttctttctt gattcaacca ggtggtaaaa acgatccagt tgctgttttc        420
gatggtgctg ttattcctgt tggtgttaac aatactccaa ctttgttgta cacttctgtt       480
tctttcttgc ctattcattg gtctattcca tatactagag ttctgaaac tcaatctttg        540 gctgttgcta gagatggtgg tagaagattc gataaattgg atcaaggtcc tgttattgct       600
gatcacccat ttgctgttga tgttactgct ttcagagatc cttttgtttt tagatccgct       660
agattggatg ttttgttgtc tttggatgaa gaggttgcta gaaatgagac tgctgttcaa       720
caagctgttg atggttggac tgaaaagaac gctccttggt acgttgctgt ttctggtggt       780
gttcatggtg ttggtccagc tcaattttg tatagacaaa acggtggtaa tgcttctgaa        840
ttccaatact gggaatattt gggtgaatgg tggcaagaag ctactaattc ttcttgggga       900
gatgagggta cttgggctgg tagatggggt tttaacttcg aaactggtaa cgttttgttt       960
ttgactgaag agggtcacga tccacaaact ggagaggttt cgttactttt gggtactgaa      1020
ggttctggtt tgcctattgt tccacaagtt tcttctattc acgatatgtt gtgggctgct      1080
ggtgaagttg gtgttggttc tgaacaagag ggtgctaagg ttgaattttc tccttctatg      1140 gctggttttct tggattgggg tttctctgct tacgctgctg ctggtaaagt tttgccagct      1200
```

-continued

```
tcttctgctg tttctaaaac ttctggtgtt gaggttgata gatacgtttc ttttgtttgg    1260
ttgactggag atcaatatga acaagctgat ggtttcccta ctgctcaaca aggttggact    1320
ggttctttgt tgttgccaag agaattgaaa gttcaaactg ttgagaacgt tgttgataat    1380
gaattggtta gagaagaggg tgtttcttgg gttgttggag agtctgataa tcaaactgct    1440
actttgagaa ctttgggtat tactattgct agagaaacta aggctgcttt gttggctaac    1500
ggttctgtta ctgctgaaga ggatagaact ttgcaaactg ctgctgttgt tcctttcgct    1560
caatctccat cttctaagtt tttcgttttg actgctcaat tggagtttcc tgcttctgct    1620
agatcctctc cattgcaatc tggtttcgaa attttggctt ctgaattgga gagaactgct    1680
atctactacc aattctctaa cgagtctttg gttgttgata gatcccaaac ttctgctgct    1740
gctcctacta acccaggttt ggattctttt actgagtctg gtaaattgag attgttcgat    1800
gttatcgaaa acggtcaaga acaagttgag actttggatt tgactgttgt tgttgataac    1860
gctgttgttg aagtttacgc taatggtaga tttgctttgt ctacttgggc tagatcctgg    1920
tacgataact ctactcaaat cagatttttc cacaatggtg aaggagaggt tcaattcaga    1980
aacgtttctg tttctgaggg tttgtataac gcttggccag aaagaaagtg a           2031
```

```
<210> SEQ ID NO 23
<211> LENGTH: 1965
<212> TYPE: DNA
<213> ORGANISM: Aspergillus japonicus

<400> SEQUENCE: 23
```

```
atgaagctca ccactaccac cctggcgctc gccaccggtg cagcagcagc agaagcctca     60
taccacctgg acaccacggc cccgccgccg accaacctca gcaccctccc caacaacacc    120
ctcttccacc tgtggcggcc gcgcgcgcac atcctgcccg ccgagggcca gatcggcgac    180
ccctgcgcgc actacaccga cccatccacc ggcctcttcc acgtggggtt cctgcacgac    240
ggggacggca tcgcgggcgc caccacggcc aacctggcca cctacaccga cacctccgat    300
aacgggagct tcctgatcca gccgggcggg aagaacgacc ccgtcgccgt gttcgacggc    360
gccgtcatcc ccgtcggcgt caacaacacc cccaccttac tctacacctc cgtctccttc    420
ctgcccatcc actggtccat cccctacacc cgcggcagcg agacgcagtc gttggccgtc    480
gcgcgcgacg gcggccgccg cttcgacaag ctcgaccagg ccccgtcat cgccgaccac    540 cccttcgccg tcgacgtcac cgccttccgc gatccgtttg tcttccgcag tgccaggttg    600
gatgtgctgc tgtcgttgga tgaggaggtg gcgcggaatg agacggccgt gcagcaggct    660
gtcgatggct ggaccgagaa gaacgccccc tggtatgtcg cggtttctgg cggggtgcac    720
ggcgtcgggc ccgcgcagtt cctctaccgc cagaacggcg ggaacgcttc cgagttccag    780
tactgggagt acctcgggga gtggtggcag gaggcgacca actccagctg gggcgacgag    840
ggcacctggg ccgggcgctg ggggttcaac ttcgagacgg ggaatgtgct cttcctcacc    900
gaggagggcc atgaccccca gacgggcgag gtgttcgtca ccctcggcac ggaggggtct    960
ggcctgccca tcgtgccgca ggtctccagt atccacgata tgctgtgggc ggcgggtgag   1020
gtcggggtgg gcagtgagca ggaggtgccc aaggtcgagt ctccccctc catggccggg   1080 tttctggact ggggggttca gcgcctacgct gcggcgggca aggtgctgcc ggccagctcg   1140
gcggtgtcga gaccagcggc gtggaggtg atcggtatg tctcgttcgt ctggttgacg   1200
ggcgaccagt acgagcaggc ggacgggttc cccacggctc agcaggggtg gacggggtcg   1260
ctgctgctgc cgcgcgagct gaaggtgcag acggtggaga acgtcgtcga caacgagctg   1320
```

-continued

```
gtgcgcgagg agggcgtgtc gtgggtggtg ggggagtcgg acaaccagac ggccacgctt    1380
cgcacgctgg ggatcacgat cgcccgggag accaaggcgg ccctgctggc caacggctcg    1440
gtgaccgcgg aggaggaccg cacgctgcag acggcggccg tcgtgccgtt cgcgcaatcg    1500
ccgagctcca agttcttcgt gctgacggcc cagctggagt tccccgcgag cgcgcgctcg    1560
tccccgctcc agtccgggtt cgaaatcctg gcgtcggagc tggagcgcac ggccatctac    1620
taccagttca gcaacgagtc gctggtcgtc gaccgcagcc agaccagtgc ggcggcgccc    1680
acgaaccccg ggctggatag ctttactgag tccggcaagt tgcggttgtt cgacgtgatc    1740
gagaacggcc aggagcaggt cgagacgttg gatctcactg tcgtcgtgga taacgcggtt    1800
gtcgaggtgt atgccaacgg cgcctttgcg ttgagcacct gggcgagatc gtggtacgac    1860
aactccaccc agatccgctt cttccacaac ggcgagggcg aggtgcagtt caggaatgtc    1920
tccgtgtcgg aggggctcta taacgcctgg ccggagagaa agtga                    1965
```

<210> SEQ ID NO 24
<211> LENGTH: 6
<212> TYPE: PRT
<213> ORGANISM: Artificial Sequence
<220> FEATURE:
<223> OTHER INFORMATION: Conserved bioactive fragment of
      fructosyltransferase of Aspergillus japonicus (Position 57-62)

<400> SEQUENCE: 24

Gln Ile Gly Asp Pro Cys
1               5

<210> SEQ ID NO 25
<211> LENGTH: 14
<212> TYPE: PRT
<213> ORGANISM: Artificial Sequence
<220> FEATURE:
<223> OTHER INFORMATION: Conserved bioactive fragment of
      fructosyltransferase of Aspergillus japonicus (Position 119-132)

<400> SEQUENCE: 25

Asp Gly Ala Val Ile Pro Val Gly Val Asn Asn Thr Pro Thr
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Conserved bioactive fragment of
      fructosyltransferase of Aspergillus japonicus (Position 320-330)

<400> SEQUENCE: 26

Ser Gly Leu Pro Ile Val Pro Gln Val Ser
1               5                   10

<210> SEQ ID NO 27
<211> LENGTH: 16
<212> TYPE: PRT
<213> ORGANISM: Artificial Sequence
<220> FEATURE:
<223> OTHER INFORMATION: Conserved bioactive fragment of
      fructosyltransferase of Aspergillus japonicus (Position 401-416)

<400> SEQUENCE: 27

Gly Asp Gln Tyr Glu Gln Ala Asp Gly Phe Pro Thr Ala Gln Gln Gly
1               5                   10                  15

NUCLEIC ACIDS, VECTORS, HOST CELLS AND METHODS FOR PRODUCTION OF FRUCTOSYLTRANSFERASE FROM *ASPERGILLUS JAPONICUS*

FIELD OF INVENTION

The present invention relates to the field of genetic engineering. More specifically, the invention is directed towards obtaining improved production of a novel recombinant fructosyltransferase, encoded by ft gene of *Aspergillus japonicus* as a secreted protein.

BACKGROUND

Fructose oligomers, also known as fructooligosaccharides (FOS) constitute a series of homologous oligosaccharides. Fructooligosaccharides are usually represented by the formula $GF_n$ and are mainly composed of 1-kestose (GF2), nystose (GF3) and β-fructofuranosylnystose (GF4), in which two, three, and four fructosyl units are bound at the β-2,1 position of glucose.

Fructooligosaccharides (FOS) are characterized by many beneficial properties such as low sweetness intensity and usefulness as a prebiotic. Due to the low sweetness intensity (about one-third to two-third as compared to sucrose) and low calorific values (approximately 0-3 kcal/g), fructooligosaccharides can be used in various kinds of food as a sugar substitute. Further, as a prebiotic, fructooligosaccharides have been reported for being used as protective agents against colon cancer, enhancing various parameters of the immune system, improving mineral adsorption, beneficial effects on serum lipid and cholesterol concentrations and exerting glycemic control for controlling obesity and diabetes (Dominguez, Ana Luísa, et al. "An overview of the recent developments on fructooligosaccharide production and applications." *Food and bioprocess technology* 7.2 (2014): 324-337.)

However, fructooligosaccharides are found only in trace amounts as natural components in fruits, vegetables, and honey. Due to such low concentration, it is practically impossible to extract fructooligosaccharides from food.

Attempts have been made to produce fructooligosaccharides through enzymatic synthesis from sucrose by microbial enzymes with transfructosylation activity. However, the major constraints in the previous attempts have been the lower catalytic efficiency, feedback inhibition of the enzyme by glucose leading lower FOS yields and the requirement of longer time periods for conversion of sucrose by the enzymes expressed in the recombinant host system. Further, industrial production of microbial enzymes exhibiting transfructosylation activity is challenging due to additional limitations associated with large scale expression of enzyme, enzyme stability, fermentation and purification processes.

Commercial-scale production of fructooligosaccharides requires identification and mass production of efficient enzymes. Due to the aforesaid limitations, the production of microbial enzymes with efficient transfructosylation activity is a costly affair which in-turn increases the production cost of fructooligosaccharides.

Thus, there is a long-felt need for identifying and providing efficient, cheap and industrially scalable means for the production of microbial enzymes with superior transfructosylation activity, which in turn lowers the cost of production of fructooligosaccharides.

SUMMARY OF THE INVENTION

Technical Problem

The technical problem to be solved in this invention is to identify and improve the yield of a novel fructosyltransferase (UniProtKB: F1ADK9_ASPJA) of *Aspergillus japonicus*.

The Solution to the Problem

The problem has been solved by overexpression of a novel fructosyltransferase of *Aspergillus japonicus* by engineering nucleic acid sequences, protein sequences, promoters, recombinant vectors, host cells and secretory signal peptides for achieving high yield of novel recombinant fructosyltransferase.

Additionally, the fermentation strategy has been modified to obtain a high yield of about 2-5 gm/L recombinant fructosyltransferase.

Overview of the Invention

The present invention relates to nucleic acids, protein sequences, vectors and host cells for recombinant expression of a novel fructosyltransferase. The present invention also relates to precursor peptides containing signal peptides fused to a novel fructosyltransferase enzymes which enable generation of higher yield of the efficient enzyme as a secretory protein.

The invention also relates to a process for the expression of a novel recombinant fructosyltransferase as a secreted protein. The fructosyltransferase concentration is found to be about 2-5 gm/L. The enzyme exhibits almost 85% purity after filtration, which eliminates the need for costly chromatographic procedures.

BRIEF DESCRIPTION OF DRAWINGS

The features of the present disclosure will become fully apparent from the following description taken in conjunction with the accompanying figures. With the understanding that the figures depict only several embodiments in accordance with the disclosure and are not to be considered limiting of its scope, the disclosure will be described further through the use of the accompanying figures.

FIG. 1 depicts the sequence alignment of the native ft gene (SEQ ID NO: 23) and the modified ft gene (SEQ ID NO: 2) encoding fructosyltransferase.

FIG. 2 represents the construction scheme of pPICZαA vector.

FIG. 5 (*a*) depicts the SDS-PAGE analysis of samples collected at different time intervals during fermentation of *Pichia pastoris* KM71H strain expressing recombinant fructosyltransferase enzyme. FIG. 5 (*b*) depicts the SDS-PAGE analysis of recombinant fructosyltransferase enzyme after purification.

BRIEF DESCRIPTION OF SEQUENCES AND SEQUENCE LISTING

Figure 3:
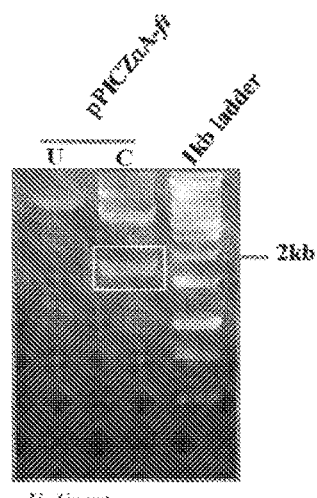
FIG. 3 depicts the results of the restriction digestion analysis performed on the recombinant plasmid pPICZαA-ft.

SEQ ID NO: 1—Amino acid sequence of novel fructo-syltransferase (654 amino acids)

SEQ ID NO: 2—Modified nucleic acid sequence of the gene encoding novel fructosyltransferase (1965 base pairs)

TABLE 1

Modified Signals Peptides used

| Sr. No. | Modified Signal Peptide (Source) | SEQ ID NO | Amino Acid Sequence | Length (a.a.) |
|---|---|---|---|---|
| 1 | FAK-Alpha-factor (*S. cerevisiae*) | SEQ ID NO: 3 | MRFPSIFTAVLFAASSALAAPVN TTTEDETAQIPAEAVIGYSDLEG DFDVAVLPFSNSTNNGLLFINTT IASIAAKEEGVSLEKR | 85 |
| 2 | FAKS-Alpha-factor full (*S. cerevisiae*) | SEQ ID NO: 4 | MRFPSIFTAVLFAASSALAAPVN TTTEDETAQIPAEAVIGYSDLEG DFDVAVLPFSNSTNNGLLFINTT IASIAAKEEGVSLEKREAEA | 89 |
| 3 | AT-Alpha-factor_T (*S. cerevisiae*) | SEQ ID NO: 5 | MRFPSIFTAVLFAASSALALEKR | 23 |
| 4 | AA-Alpha-amylase (*Aspergillus niger*) | SEQ ID NO: 6 | MVAWWSLFLYGLQVAAPALALEK R | 24 |
| 5 | GA-Glucoamylase (*Aspergillus awamori*) | SEQ ID NO: 7 | MSFRSLLALSGLVCSGLALEKR | 22 |
| 6 | IN-Inulinase (*Kluyveromyces maxianus*) | SEQ ID NO: 8 | MKLAYSLLLPLAGVSALEKR | 20 |
| 7 | IV-Invertase (*S. cerevisiae*) | SEQ ID NO: 9 | MLLQAFLFLLAGFAAKISALEKR | 23 |
| 8 | KP-Killer protein (*S. cerevisiae*) | SEQ ID NO: 10 | MTKPTQVLVRSVSILFFITLLHL VVALEKR | 30 |
| 9 | LZ-Lysozyme (*Gallus gallus*) | SEQ ID NO: 11 | MLGKNDPMCLVLVLLGLTALLGI CQGLEKR | 30 |
| 10 | SA-Serum albumin (*Homo sapiens*) | SEQ ID NO: 12 | MKWVTFISLLFLFSSAYSLEKR | 22 |

In all the secretory signal peptide sequences, a stretch of four amino acids (LEKR) was added for the efficient Kex2 processing of pre-protein.

TABLE 2

Modified nucleic acid sequences of fructosyltransferase (ft) gene fused to signal peptides

| Sr. No. | Description | SEQ ID NO | Length (b.p.) |
|---|---|---|---|
| 1 | FAK—Alpha-factor of *S. cerevisiae* fused to modified nucleic acid of fructosyltransferase (ft) gene | SEQ ID NO: 13 | 2220 |
| 2 | FAKS—Alpha-factor full of *S. cerevisiae* fused to modified nucleic acid of fructosyltransferase (ft) gene | SEQ ID NO: 14 | 2232 |
| 3 | AT—Alpha-factor_T of *S. cerevisiae* fused to modified nucleic acid of fructosyltransferase (ft) gene | SEQ ID NO: 15 | 2034 |
| 4 | AA—Alpha-amylase of *Aspergillus niger* fused to modified nucleic acid of fructosyltransferase gene | SEQ ID NO: 16 | 2037 |
| 5 | GA—Glucoamylase of *Aspergillus awamori* fused to modified nucleic acid of fructosyltransferase (ft) gene | SEQ ID NO: 17 | 2031 |

TABLE 2-continued

Modified nucleic acid sequences of fructosyltransferase (ft) gene fused to signal peptides

| Sr. No. | Description | SEQ ID NO | Length (b.p.) |
|---|---|---|---|
| 6 | IN—Inulinase of *Kluyveromyces maxianus* fused to modified nucleic acid of fructosyltransferase (ft) gene | SEQ ID NO: 18 | 2025 |
| 7 | IV—Invertase of *S. cerevisiae* fused to modified nucleic acid of fructosyltransferase (ft) gene | SEQ ID NO: 19 | 2034 |
| 8 | KP—Killer protein of *S. cerevisiae* fused to modified nucleic acid of fructosyltransferase (ft) gene | SEQ ID NO: 20 | 2055 |
| 9 | LZ—Lysozyme of *Gallus gallus* fused to modified nucleic acid of fructosyltransferase (ft) gene | SEQ ID NO: 21 | 2055 |
| 10 | SA—Serum albumin of *Homo sapiens* fused to modified nucleic acid of fructosyl-transferase (ft) gene | SEQ ID NO: 22 | 2031 |

SEQ ID NO: 23—Native nucleic acid sequence of the ft gene (1965 base pairs) encoding secreted fructosyltransferase.

TABLE 3

| Position | Fragment | SEQ ID Number |
|---|---|---|
| | Bioactive fragments of fructosyltransferase (ft) gene are conserved and accounts for the catalytic activities | |
| 57-62 | QIGDPC | SEQ ID NO: 24 |
| 119-132 | DGAVIPVGVNNTPT | SEQ ID NO: 25 |
| 320-330 | SGLPIVPQVS | SEQ ID NO: 26 |
| 401-416 | GDQYEQADGFPTAQQG | SEQ ID NO: 27 |

Definitions

Unless defined otherwise, all technical and scientific terms used herein have the same meaning as commonly understood by one of ordinary skill in the art to which the methods belong. Although any vectors, host cells, methods and compositions similar or equivalent to those described herein can also be used in the practice or testing of the vectors, host cells, methods and compositions, representative illustrations are now described.

Where a range of values are provided, it is understood that each intervening value between the upper and lower limit of that range and any other stated or intervening value in that stated range, is encompassed within by the methods and compositions. The upper and lower limits of these smaller ranges may independently be included in the smaller ranges and are also encompassed within by the methods and compositions, subject to any specifically excluded limit in the stated range. Where the stated range includes one or both of the limits, ranges excluding either or both of those included limits are also included in the methods and compositions.

It is appreciated that certain features of the methods, which are, for clarity, described in the context of separate embodiments, may also be provided in combination in a single embodiment. Conversely, various features of the methods and compositions, which are, for brevity, described in the context of a single embodiment, may also be provided separately or in any suitable sub-combination. It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

As will be apparent to those of skill in the art upon reading this disclosure, each of the individual embodiments described and illustrated herein has discrete components and features which may be readily separated from or combined with the features of any of the other embodiments without departing from the scope or spirit of the present methods. Any recited method can be carried out in the order of events recited or in any other order that is logically possible.

The term "host cell(s)" includes an individual cell or cell culture which can be, or has been, a recipient for the subject of expression constructs. Host cells include progeny of a single host cell. Host cells for the purposes of this invention refers to any strain of *Pichia pastoris* which can be suitably used for the purposes of the invention. Examples of strains that can be used for the purposes of this invention include wild type, mut+, mut S, mut– strains of *Pichia* such as KM71H, KM71, SMD1168H, SMD1168, GS115, X33.

The term "recombinant strain" or "recombinant host cell(s)" refers to a host cell(s) which has been transfected or transformed with the expression constructs or vectors of this invention.

The term "expression vector" refers to any vector, plasmid or vehicle designed to enable the expression of an inserted nucleic acid sequence following transformation into the host.

The term "promoter" refers to DNA sequences that define where transcription of a gene begins. Promoter sequences are typically located directly upstream or at the 5' end of the transcription initiation site. RNA polymerase and the necessary transcription factors bind to the promoter sequence and initiate transcription. Promoters can either be constitutive or inducible promoters. Constitutive promoters are the promoter which allows continual transcription of its associated genes as their expression is normally not conditioned by environmental and developmental factors. Constitutive promoters are very useful tools in genetic engineering because constitutive promoters drive gene expression under inducer-free conditions and often show better characteristics than commonly used inducible promoters. Inducible promoters are the promoters that are induced by the presence or absence of biotic or abiotic and chemical or physical factors. Inducible promoters are a very powerful tool in genetic engineering because the expression of genes operably linked to them can be turned on or off at certain stages of development or growth of an organism or in a particular tissue or cell type.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter).

The term "transcription" refers to the process of making an RNA copy of a gene sequence. This copy, called a messenger RNA (mRNA) molecule, leaves the cell nucleus and enters the cytoplasm, where it directs the synthesis of the protein, which it encodes.

The term "translation" refers to the process of translating the sequence of a messenger RNA (mRNA) molecule to a sequence of amino acids during protein synthesis. The genetic code describes the relationship between the sequence of base pairs in a gene and the corresponding amino acid sequence that it encodes. In the cell cytoplasm, the ribosome reads the sequence of the mRNA in groups of three bases to assemble the protein.

The term "expression" refers to the biological production of a product encoded by a coding sequence. In most cases, a DNA sequence, including the coding sequence, is transcribed to form a messenger-RNA (mRNA). The messenger-RNA is then translated to form a polypeptide product that has a relevant biological activity. Also, the process of expression may involve further processing steps to the RNA product of transcription, such as splicing to remove introns, and/or post-translational processing of a polypeptide product.

The term "modified nucleic acid" as used herein is used to refer to a nucleic acid encoding fructosyltransferase fused to a signal peptide. In embodiments, the modified nucleic acid is represented by SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO: 21, SEQ ID NO: 22 or a functionally equivalent variant thereof. The functional variant includes any nucleic acid having substantial or significant sequence identity or similarity to SEQ ID NO:13-22, and which retains the biological activities of the same.

The terms "polypeptide", "peptide" and "protein" are used interchangeably herein to refer to two or more amino acid residues joined to each other by peptide bonds or modified peptide bonds. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer. "Polypeptide" refers to both short chains, commonly referred to as peptides, oligopeptides or oligomers, and to longer chains, generally referred to as proteins. Polypeptides may contain amino acids other than the 20 gene-encoded amino acids. Likewise, "protein" refers to at least two covalently attached amino acids, which includes proteins, polypeptides, oligopeptides, and peptides. A protein may be made up of naturally occurring amino acids and peptide bonds, or synthetic peptidomimetic structures. Thus "amino acid", or "peptide residue", as used herein means both naturally occurring and synthetic amino acids. "Amino acid" includes imino acid residues such as proline and hydroxyproline. The side chains may be in either the (R) or the (S) configuration.

The term "signal peptide" or "signal peptide sequence" is defined herein as a peptide sequence usually present at the N-terminal end of newly synthesized secretory or membrane polypeptides which directs the polypeptide across or into a cell membrane of the cell (the plasma membrane in prokaryotes and the endoplasmic reticulum membrane in eukaryotes). It is usually subsequently removed. In particular said signal peptide may be capable of directing the polypeptide into a cell's secretory pathway.

The term "precursor peptide" as used herein refers to a peptide comprising a signal peptide (also known as leader sequences) operably linked to the fructosyltransferase of *Aspergillus japonicus*. The signal peptides are cleaved off during post-translational modifications inside the *Pichia* host cells and the mature fructosyltransferase (SEQ ID NO: 1) is released into the medium.

The term "variant" as used herein in reference to precursor peptides/proteins refers to peptides with amino acid substitutions, additions, deletions or alterations that do not substantially decrease the activity of the signal peptide or the enzyme. Variants include a structural as well as functional variants. The term variant also includes the use of a substituted amino acid in place of an unsubstituted parent amino acid.

Amino acid substitution tables providing functionally similar amino acids are well known to one of ordinary skill in the art. The following six groups are examples of amino acids that are considered to be variants for one another:

TABLE 4

| Amino acid substitution table | |
| --- | --- |
| | Amino acids |
| Group 1 | Alanine (A), Serine (S), Threonine (T), Glycine (G), Proline (P) |
| Group 2 | Aspartic acid (D), Glutamic acid (E), Asparagine (N), Glutamine (Q) |
| Group 3 | Arginine (R), Lysine (K), Histidine (H) |
| Group 4 | Isoleucine (I), Leucine (L), Methionine (M), Valine (V) |
| Group 5 | Phenylalanine (F), Tyrosine (Y), Tryptophan (W) |
| Group 6 | Cysteine (C) |

Detailed Description of the Invention

The present invention discloses nucleic acids, vectors and recombinant host cells for efficient production of biologically active and soluble recombinant fructosyltransferase of *Aspergillus japonicus* as a secreted protein. Further, the invention provides a process for commercial-scale production of recombinant fructosyltransferase.

The invention contemplates a multidimensional approach for achieving a high yield of novel recombinant fructosyltransferase in a heterologous host. The native gene for fructosyltransferase has been modified for expression in *Pichia pastoris*. Further, the modified gene has been fused to one or more signal peptides.

In one embodiment, the modified nucleic acid encoding novel fructosyltransferase of *Aspergillus japonicus* is represented by SEQ ID NO: 2.

In another embodiment, the modified nucleic acid is fused to one or more signal peptide.

In another embodiment, the signal peptide is selected from Alpha-factor of *S. cerevisiae* (FAK), Alpha-factor full of *S. cerevisiae* (FAKS) of *S. cerevisiae*, Alpha factor_T of *S. cerevisiae* (AT), Alpha-amylase of *Aspergillus niger* (AA), Glucoamylase of *Aspergillus awamori* (GA), Inulinase of *Kluyveromyces maxianus* (IN), Invertase of *S. cerevisiae* (IV), Killer protein of *S. cerevisiae* (KP), Lysozyme of *Gallus gallus* (LZ), Serum albumin of *Homo sapiens* (SA).

In another embodiment, the signal peptide are provided in the below Table 5.

TABLE 5

| Signal peptides | | | |
| --- | --- | --- | --- |
| Sr. No. | Signal Peptides (Source) | Amino Acid Sequence | Length (a.a.) |
| 1 | FAK-Alpha-factor (*S. cerevisiae*) | MRFPSIFTAVLFAASSALAAPVNTTTEDE TAQIPAEAVIGYSDLEGDFDVAVLPFSNS TNNGLLFINTTIASIAAKEEGVS | 81 |

TABLE 5-continued

| Signal peptides | | |
|---|---|---|
| Sr. No. | Signal Peptides (Source) | Amino Acid Sequence | Length (a.a.) |

| Sr. No. | Signal Peptides (Source) | Amino Acid Sequence | Length (a.a.) |
|---|---|---|---|
| 2 | AT-Alpha-factor_T (*S. cerevisiae*) | MRFPSIFTAVLFAASSALA | 19 |
| 3 | AA-Alpha-amylase (*Aspergillus niger*) | MVAWWSLFLYGLQVAAPALA | 20 |
| 4 | GA-Glucoamylase (*Aspergillus awamori*) | MSFRSLLALSGLVCSGLA | 18 |
| 5 | IN-Inulinase (*Kluyveromyces maxianus*) | MKLAYSLLLPLAGVSA | 16 |
| 6 | IV-Invertase (*S. cerevisiae*) | MLLQAFLFLLAGFAAKISA | 19 |
| 7 | KP-Killer protein (*S. cerevisiae*) | MTKPTQVLVRSVSILFFITLLHLVVA | 26 |
| 8 | LZ-Lysozyme (*Gallus gallus*) | MLGKNDPMCLVLVLLGLTALLGICQG | 26 |
| 9 | SA-Serum albumin (*Homo sapiens*) | MKWVTFISLLFLFSSAYS | 18 |

In another embodiment, the signal peptide is selected from a list of modified signal peptides as described in Table 1.

In another embodiment, the nucleic acid fused to one or more modified signal peptide is selected from a group comprising SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22 and variants thereof.

In another embodiment, the modified nucleic acid is cloned in an expression vector.

In another embodiment, the expression vector is configured for secretory or intracellular expression of recombinant fructosyltransferase from *Aspergillus japonicus*.

In yet another embodiment, the expression vector is selected from a group comprising pPICZαA, pPICZαB, pPICZαC, pGAPZαA, pGAPZαB, pGAPZαC, pPIC3, pPIC3.5, pPIC3.5K, PA0815, pPIC9, pPIC9K, IL-D2 and pHIL-S1.

The expression of the modified fructosyltransferase (ft) gene fused to a signal peptide is preferably driven by a constitutive or inducible promoter.

In another embodiment, the nucleic acid to be expressed in operably linked to the promoter.

In another embodiment, the constitutive or inducible promoter is selected from a group listed in Table 6.

TABLE 6

| List of promoters used | | | | | |
|---|---|---|---|---|---|
| Sr. No. | Promoter Type | Gene Name | Gene Product | Inducer | Expression Level |
| 1 | Inducible | AOX1 | Alcohol oxidase 1 | Methanol | Strong |
| 2 | Inducible | ADH3 | Alcohol dehydrogenase | Ethanol | Strong |
| 3 | Inducible | DAS | Dihyroxyacetone phosphate | Methanol | Strong |
| 4 | Inducible | FLD1 | Formaldehyde dehydrogenase | Methanol/ Methylamine | Strong |
| 5 | Inducible | LRA3 | L-rhamnonate dehydratase | Rhamnose | 75% of pGAP |
| 6 | Inducible | THI11 | Thiamine Biosynthesis Protein | Repressed by Thiamine | 70% of pGAP |
| 7 | Constitutive | GAP | Glyceraldehyde 3-phosphatedehydrogenate | — | strong |
| 8 | Constitutive | YPT1 | GPTase involved in sectetion | — | weak |
| 9 | Constitutive | TEF1 | Translation elongation factor 1 alpha | — | strong |
| 10 | Constitutive | GCW14 | Glycosylphosphatidylinositol | — | strong |
| 11 | Constitutive | PGK1 | Phosphoglycerate kinase | — | 10% of pGAP |

In another embodiment, the promoter is an AOX1 promoter, which is induced by methanol and repressed by glucose.

In an embodiment, the expression vector containing the modified gene of interest (fructosyltransferase gene fused to a nucleic acid encoding signal peptide) is transformed in an appropriate host.

In another embodiment, the expression vector containing the gene of interest is transformed in yeast cells.

In another embodiment, the yeast cell is a *Pichia pastoris*.

In yet another embodiment, the *Pichia Pastoris* host cell is a mut+, mut S or mut– strains. Mut+ represents methanol utilization plus phenotype.

In yet another embodiment, the *Pichia Pastoris* host cell strain is selected from a group comprising KM71H, KM71, SMD1168H, SMD1168, GS115, X33.

In another embodiment, the invention provides fructosyltransferase precursor peptides, wherein fructosyltransferase of *Aspergillus japonicus* is fused to one or more signal peptide.

In another embodiment, fructosyltransferase of *Aspergillus japonicus* has the amino acid sequence set forth in SEQ ID NO:1 and functional variants thereof. Functional variant includes any protein sequence having substantial or significant sequence identity or similarity to SEQ ID NO:1 and or having a substantial or significant structural identity or similarity to SEQ ID NO:1, and which retains the biological activities of the same.

In another embodiment, the signal peptide is selected from a group comprising Alpha-factor full of *S. cerevisiae* (FAK) set forth in SEQ ID NO: 3, Alpha-factor full of *S. cerevisiae* (FAKS) set forth in SEQ ID NO: 4, Alpha factor_T of *S. cerevisiae* (AT) set forth in SEQ ID NO: 5, Alpha-amylase of *Aspergillus niger* (AA) set forth in SEQ ID NO: 6, Glucoamylase of *Aspergillus awamori* (GA) set forth in SEQ ID NO: 7, Inulinase of *Kluyveromyces maxianus* (IN) set forth in SEQ ID NO: 8, Invertase of *S. cerevisiae* (IV) set forth in SEQ ID NO: 9, Killer protein of *S. cerevisiae* (KP) set forth in SEQ ID NO: 10, Lysozyme of *Gallus gallus* (LZ) set forth in SEQ ID NO: 11, Serum albumin of *Homo sapiens* (SA) set forth in SEQ ID NO: 12, and variants thereof.

In an embodiment, the process for the production of recombinant fructosyltransferase of *Aspergillus japonicus* is provided.

Aspects of the present invention relate to fermentation of recombinant *Pichia pastoris* cells containing modified recombinant fructosyltransferase (ft) gene. After completion of the fermentation, the fermentation broth is subjected to centrifugation and filtered using microfiltration and the recombinant enzyme is separated. The recovered recombinant enzyme is concentrated using Tangential Flow Ultrafiltration or evaporation and finally the concentrated enzyme is formulated.

In one embodiment, the process for expressing fructosyltransferase of *Aspergillus japonicus* at high levels comprises the steps of:

a. culturing recombinant host cells in a suitable fermentation medium to obtain recombinant fructosyltransferase enzyme secreted into fermentation broth;

b. harvesting supernatant from the fermentation broth, wherein the supernatant contains recombinant fructosyltransferase; and c. purifying recombinant fructosyltransferase.

In another embodiment, the fermentation medium is basal salt medium as described in Table 7.

In yet another embodiment, the supernatant from the fermentation broth is harvested using centrifugation.

In one embodiment, the percentage of inoculum or starter culture to initiate the fermenter culture is in the range of 2.0% to 15.0% (v/v).

In another embodiment, the pH of the fermentation medium is maintained in the range of 4.0 to 7.5 as the secreted enzyme undergoes proper folding and is biologically active at this pH range.

In yet another embodiment, the temperature of the fermentation process is in the range of 15° C. to 40° C.

In another embodiment, the time for fermentation process is in the range of 50-150 hrs. In a further, embodiment, the fermentation broth is centrifuged at a speed in the range from 2000×g to 15000×g using continuous online centrifugation.

The supernatant obtained after centrifugation is subjected to microfiltration and purified to recover biologically active recombinant fructosyltransferase.

In one embodiment, the supernatant obtained after centrifugation is concentrated using a Tangential Flow Filtration based Ultra filtration System.

The cut-off size of the membranes used in Tangential Flow Filtration (TFF) systems that may be used to remove impurities and to concentrate the collected culture supernatant may range between 5 to 100 kDa.

In another embodiment, no centrifugation is required for the process due to the high yield and purity of the secreted enzyme.

The fructosyltransferase concentration obtained in this invention is found to be in the range of 2-5 gm/L and the purity is about 85%.

EXAMPLES

The following examples particularly describe the manner in which the invention is to be performed. But the embodiments disclosed herein do not limit the scope of the invention in any manner.

Example 1: Modified Nucleic Acids for Expression of Recombinant Fructosyltransferase of *Aspergillus japonicus* in *Pichia pastoris*

The cDNA of the native fructosyltransferase (ft) of *Aspergillus japonicus* is represented by SEQ ID NO: 23 and the amino acid sequence of novel fructosyltransferase is represented by SEQ ID NO: 1.

The native cDNA was modified for maximizing expression in *Pichia pastoris*. The modified nucleic acid is represented by SEQ ID NO: 2. The differences between the native and the modified sequence is depicted in FIG. 1.

An expression cassette encoding the fructosyltransferase was modified for maximizing expression in *Pichia pastoris*. The modified open reading frame contains the modified nucleotide sequence (SEQ ID NO: 2) encoding fructosyltransferase fused to a signal peptide.

The nucleic acids have been designed such that the encoded signal peptides contain an additional stretch of four amino acids (LEKR) for the efficient Kex2 processing of precursor peptide.

The preferred codons for expression in *Pichia pastoris* have been used in place of rare codons.

The nucleotide sequence of the modified open reading frames encoding for fructosyltransferase fused with modified signal peptides are given below:

Alpha-factor of *S. cerevisiae* (FAK) is represented by SEQ ID NO: 13

Alpha-factor full of *S. cerevisiae* (FAKS) is represented by SEQ ID NO: 14

Alphafactor_T of *S. cerevisiae* (AT) represented by SEQ ID NO: 15

Alpha-amylase of *Aspergillus niger* (AA) represented by SEQ ID NO: 16

Glucoamylase of *Aspergillus awamori* (GA) represented by SEQ ID NO: 17

Inulinase of *Kluyveromyces maxianus* (IN) represented by SEQ ID NO: 18

Invertase of *S. cerevisiae* (IV) represented by SEQ ID NO: 19

Killer protein of *S. cerevisiae* (KP) represented by SEQ ID NO: 20

Lysozyme of *Gallus gallus* (LZ) represented by SEQ ID NO: 21

Serum albumin of *Homo sapiens* (SA) represented by SEQ ID NO: 22.

The SEQ ID NO: 13 nucleic acid sequence was chemically synthesized cloned into pPICZαA vector and remaining modified nucleic acid sequences have been generated by overlap extension PCR using SEQ ID NO: 13 expression cassette as a template.

Example 2: Polypeptide Sequences of Fructosyltransferase Fused to Signal Peptides Recombinant precursor proteins were obtained by translating the gene encoding for fructosyltransferase of *Aspergillus japonicus* fused with signal peptides.

The signal peptides used in the modified precursor peptides were Alpha-factor of *S. cerevisiae* (FAK) represented by SEQ ID NO: 3, Alpha-factor full of *S. cerevisiae* (FAKS) represented by SEQ ID NO: 4, Alpha-factor_T of *S. cerevisiae* (AT) represented by SEQ ID NO: 5, Alpha-amylase of *Aspergillus niger* (AA) represented by SEQ ID NO: 6, Glucoamylase of *Aspergillus awamori* (GA) represented by SEQ ID NO: 7, Inulinase of *Kluyveromyces maxianus* (IN) represented by SEQ ID NO: 8, Invertase of *S. cerevisiae* (IV) represented by SEQ ID NO: 9, Killer protein of *S. cerevisiae* (KP) represented by SEQ ID NO: 10, Lysozyme of *Gallus gallus* (LZ) represented by SEQ ID NO: 11 and Serum albumin of *Homo sapiens* (SA) represented by SEQ ID NO: 12. The modified signal peptides contain an additional stretch of four amino acids (LEKR) for the efficient Kex2 processing of precursor peptide.

The signal peptides are cleaved off during post-translational modifications inside the *Pichia* host cells and the mature recombinant fructosyltransferase comprising the amino acid sequence of SEQ ID NO: 1 is released into the medium.

Example 3: Development of Recombinant Host Cells by Transformation with Recombinant Plasmids The vector used in the process was pPICZαA. The vectors contained the modified open reading frames as described in Example 1 and an inducible promoter, AOX1. The modified sequence encoding for the recombinant protein was cloned into the pPICZαA vector.

The modified nucleic acid SEQ ID NO: 2 encoding fructosyltransferase (ft) gene was cloned between XhoI/SacII restriction sites present in the MCS of pPICZαA vector to bring signal sequence Alpha-factor of *S. cerevisiae*

(FAK) in frame to create SEQ ID NO: 13 expression cassette using regular molecular biology procedures. The vector map for pPICZαA is represented in FIG. 2.

The putative recombinant plasmids were selected on low salt-LB media containing 25 µg/ml Zeocin and screened by XhoI/SacII restriction digestion analysis.

The recombinant plasmid pPICZαA ft was confirmed by XhoI/SacII restriction digestion analysis which resulted in release of 1980 bp fragment. The results of the restriction digestion analysis are depicted in FIG. 3.

Thereafter, *Pichia pastoris* KM71H cells were electroporated with linearized recombinant pPICZαA-ft DNA. The *Pichia* integrants were selected on yeast extract peptone dextrose sorbitol agar (YPDSA) containing 100 µg/ml Zeocin.

The integration was screened with colony PCR (cPCR). For cPCR, a template from each of the *Pichia* integrants was generated by the alkali lysis method.

The *Pichia* integrants were grown for 48 h in BMD1 media and further induced first with BMM2 and then successively with BMM10 media which provided final concentration of 0.5% methanol in the culture medium. At the end of 96 hrs induction period, culture supernatants from different clones were harvested. Total protein from each of the harvested supernatants was precipitated with 20% TCA and analyzed on SDS-PAGE.

Figure 4:
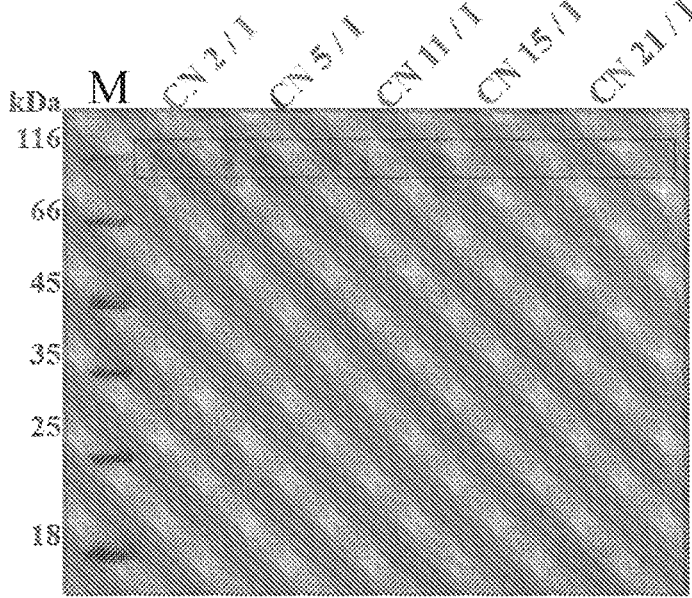
FIG. 4 depicts the expression of fructosyltransferase upon induction from the recombinant *Pichia pastoris* host cells.

Upon induction fructosyltransferase protein bands were seen at the size of approximately 110 kDa as depicted in FIG. 4.

The calculated molecular weight was about 70.85 kDa. The increase in molecular weight may have been contributed by glycosylation.

Example 4: Fermentation of Recombinant *Pichia pastoris* Expressing Fructosyltransferase of *Aspergillus japonicus*

Fermentation of recombinant *Pichia pastoris* cells containing the modified fructosyltransferase (ft) gene as described in Example 1 was carried out in a 50 L fermenter. Fermentation was carried out in basal salt medium as described herein. The recombinant host selected was KM71H, which is a mut S strain that metabolizes methanol in a slow manner.

Preparation of Pre-Seed and Seed Inoculum:

The pre-seed was generated by inoculating from the glycerol stock in 25 mL of sterile YEPG medium and growing at 30° C. in a temperature-controlled orbital shaker overnight. For generating seed, the inoculum was grown in Basal salt medium in baffled shake flasks at 30° C. in a temperature-controlled orbital shaker till $OD_{600}$ of 15-25 was reached.

Fermentation Process

The entire process of fermentation from the inoculation of fermenter with seed culture to final harvesting took about 130 hrs. Basal salt medium was prepared and sterilized in situ in the fermenter.

The composition of basal salt medium optimized for the fermentation process is provided in Table 7.

TABLE 7

| Composition of basal salt medium | |
| --- | --- |
| Component | Concentration |
| Calcium Sulphate | 1.4 gm/L |
| Potassium Sulphate | 18.6 gm/L |

TABLE 7-continued

| Composition of basal salt medium | |
| --- | --- |
| Component | Concentration |
| Magnesium Sulphate · 7H$_2$O | 16.4 gm/L |
| Glycerol | 25 gm/L |
| Potassium Di hydrogen Phosphate | 5 gm/L |
| Ammonium Sulphate | 5 mL |
| Sodium Citrate Di Hydrate | 5 gm/L |
| PTM2 | 4 mL |
| Biotin (20 mg/100 ml) | 4 mL |

*Pichia* Trace Minerals (PTM) salt solution was prepared as described in Table 8. PTM salts were dissolved and made up to 1 L volume and filter sterilized. PTM salt solution was included at the rate of 4 ml per liter of initial media volume after sterilization of the basal salt media.

TABLE 8

| PTM trace salts | |
| --- | --- |
| Cupric sulfate · 5H$_2$O | 2.0 gm/L |
| Sodium iodide | 0.08 gm/L |
| Manganese sulfate · H$_2$O | 3.0 gm/L |
| Sodium molybdate · 2H$_2$O | 0.2 gm/L |
| Boric Acid | 0.02 gm/L |
| Cobalt chloride | 0.5 gm/L |
| Zinc Sulphate | 7.0 gm/L |
| Ferrous sulfate · 7H$_2$O | 22.0 gm/L |
| Potassium chloride | 0.37 gm/L |
| Sulfuric Acid | 1 mL |
| Ferric chloride | 0.811 gm/L |
| Nickel chloride | 1.18 gm/L |
| Magnesium sulfate | 1.23 gm/L |

Growth Phase:

The growth phase starts by inoculating basal salt medium in 50 L fermenter with 5% seed culture and continues for about 24 hours. The dissolved oxygen (DO) levels were continuously monitored and never allowed to drop below 40%.

After 18 h, a DO spike was observed indicating the depletion of carbon source (Glycerol). A glycerol fed-batch was initiated by feeding 50% Glycerol (with 12 ml of PTM salts per liter of feed) for about six hours till the OD$_{600}$ reached 200.

Induction Phase:

Once sufficient biomass was generated, the induction phase was initiated by discontinuing glycerol feed and starting methanol feed. Methanol (supplemented with 12 ml of PTM salts per liter of feed) was fed at the rate of 0.5 g to 3 g per liter of initial fermentation volume. The DO was maintained at 40% and methanol feed was accordingly adjusted.

The induction of fructosyltransferase (ft) gene was monitored periodically by analyzing culture supernatant by enzyme activity assay. The induction phase was continued for about 100 hours till the OD$_{600}$ reached 600 and wet biomass reached ~540 grams per liter of culture broth.

The fermentation was stopped after 130 hours and enzyme activity in the fermenter broth at the end of fermentation was determined to be 9545 units by DNS method (Miller, 1959). One unit is defined as the amount of enzyme required to release one micromole of reducing sugars (glucose equivalents) from 10% sucrose solution in 100 mM citrate buffer pH 5.5 at 55° C. The total amount of recombinant fructosyltransferase in the culture broth was estimated by Bradford assay.

Fermentation Conditions:

The fermentation parameters considered were as given in Table 9. These essential parameters were monitored during the fermentation process.

TABLE 9

| Fermentation Parameters | | |
| --- | --- | --- |
| Fermentation parameters | Growth phase | Induction phase |
| Media | Basal Salt Media | Basal Salt Media |
| pH | 5 | 5 |
| Temperature | 30 | 25 |
| Agitation (tip speed) | 1.2-2.5 m/Sec | 2.5 m/Sec |
| Aeration | 0.5-1.5 vvm | 1.5 vvm |
| Dissolved oxygen | Minimum 40% | Minimum 40% |
| Back pressure | 0.5 kg/cm$^2$ | 0.5 kg/cm$^2$ |

Example 5: Cell Harvesting and Purification

Harvesting of the enzyme is performed by continuous centrifugation at 8000 RPM. Clear supernatant obtained after centrifugation was subjected to microfiltration using 0.1 microns cut off spiral wound TFF membrane. The filtrate is further subjected to ultrafiltration and diafiltration using 10 kDa cutoff spiral wound TFF membrane and sufficiently concentrated and to reach the desired activity. The enzyme was formulated by including 35-50% of glycerol and food-grade preservatives in the final preparation. The final purity of the enzyme was observed to be 85% as determined by SDS-PAGE analysis.

FIG. 5 (*a*) depicts the SDS-PAGE analysis of samples collected at different time intervals during fermentation of *Pichia pastoris* KM71H strain expressing recombinant fructosyltransferase enzyme. FIG. 5 (*b*) depicts the SDS-PAGE analysis of recombinant fructosyltransferase enzyme after purification.

The fructosyltransferase concentration was found to be about 2.1 gm/L. In most of the batches, the concentration was 2-5 gm/L. The purity of the recombinant fructosyltransferase was observed to be about 85%.

Example 6: Estimation of Fructosyltransferase Activity

Studies were conducted to estimate the activity of fructosyltransferase. For the estimation studies, the amount of reducing sugar generated due to the action of fructosyltransferase enzyme was calculated using DNS (3,5 Dinitrosalicylic acid) method (G. L. Miller, "Use of dinitrosalicylic acid reagent for determination of reducing sugar", Anal. Chem., 1959, 31, 426-428).

For conducting the enzyme activity assay, 10% Sucrose (dissolved in 100 mM Citrate buffer) was used as the substrate. Fructosyltransferase was recovered from the fermentation broth and processed through ultra-filtration. The ultra-filtered sample then diluted 25,000× by serial dilution in 100 mM Citrate buffer and was used. The reaction volume was 2.5 mL. The pH was maintained at 5.5 and the reaction was continued for 15 minutes.

After incubation 3 mL of DNS (3,5 Dinitrosalicylic acid) was added to each reaction mixture and boiled for 10 min, cooled and read absorbance at 540 nm, spectrophotometrically.

Figure 6:
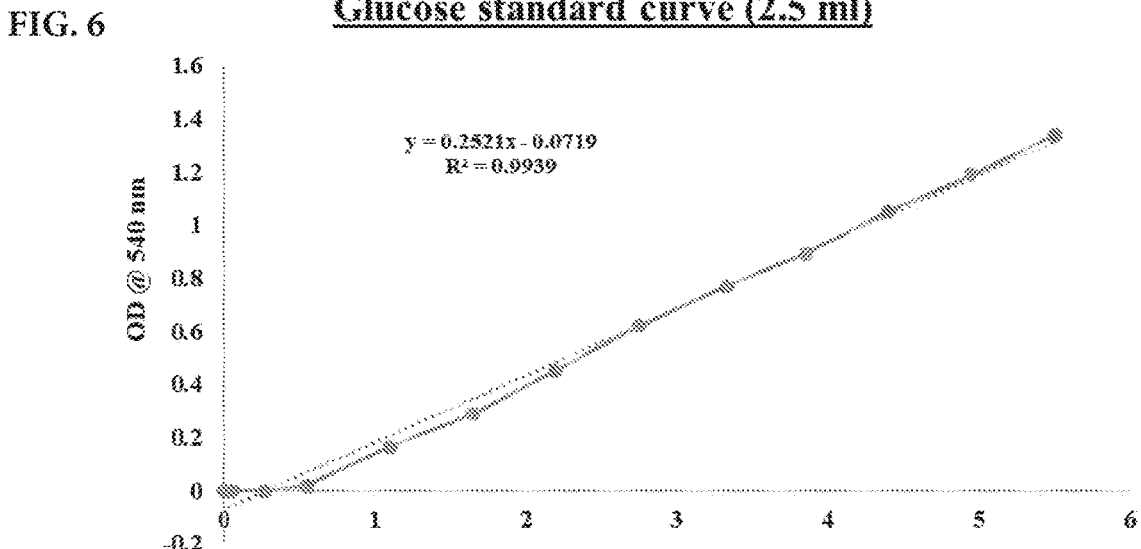
FIG. 6 depicts the Glucose standard curve used for the estimation of the activity of fructosyltransferase enzyme.

The OD of glucose at different concentration was measured as shown in Table 10 and depicted in FIG. 6. Thereafter, based on the absorbance measurement after the reaction, the enzyme activity was calculated as shown in Table 11. FIG. 6 depicts the Glucose standard curve used for the estimation of the activity of fructosyltransferase enzyme.

TABLE 10

OD measurement of glucose at different concentration

| Glucose($\mu$mol) | OD at 540 nm | Glucose($\mu$mol) | OD at 540 nm |
|---|---|---|---|
| 0 | 0 | 2.75 | 0.619 |
| 0.055 | 0 | 3.33 | 0.77 |
| 0.55 | 0.018 | 3.85 | 0.891 |
| 1.1 | 0.165 | 4.44 | 1.052 |
| 1.65 | 0.289 | 4.95 | 1.198 |
| 2.2 | 0.452 | 5.5 | 1.338 |

TABLE 11

Estimation of activity of fructosyltransferase

| Reaction test tubes | Buffer (mL) | Substrate (mL) | Enzyme (mL) | OD @ 540 nm | Effective OD | Unit/ mL |
|---|---|---|---|---|---|---|
| Reagent blank | 2.5 | — | — | 0.000 | — | — |
| Substrate blank | 0.1 | 2.4 | — | 0.31 | — | — |
| Enzyme blank | 2.4 | — | 0.1 (25,000× diluted) | 0.000 | — | — |
| Enzyme Reaction | — | 2.4 | 0.1 (25,000× diluted) | 0.96 | 0.65 | 47725 |

Example 7: Generation of Fructooligosaccharides (FOS) from Sucrose and Recombinant Fructosyltransferase Enzyme Studies were conducted to understand the ability of the enzyme in the formation of fructooligosaccharides. A 100 mL solution of 80% (w/v) sucrose was prepared in 150 mM sodium citrate buffer pH 5.5. To this, 104.7 $\mu$L of fructosyltransferase enzyme having 47725 Unit/ml of activity (equivalent to total of 5000 Units of enzyme), was added.

The reaction was set up in a 250 mL conical flask and incubated at 65° C. and 220 rpm. At regular time intervals, samples were taken and analyzed on Thin Layer Chromatographic (TLC) plates.

Glucose, sucrose, fructose and FOS (containing kestose, nystose and fructofuranosylnystose) were used as standards for the thin layer chromatographic analysis. The mobile phase used was n-Butanol: Glacial acetic acid: Water (4:2:2 v/v) and the developing/staining solution used was urea phosphoric acid.

Figure 7:
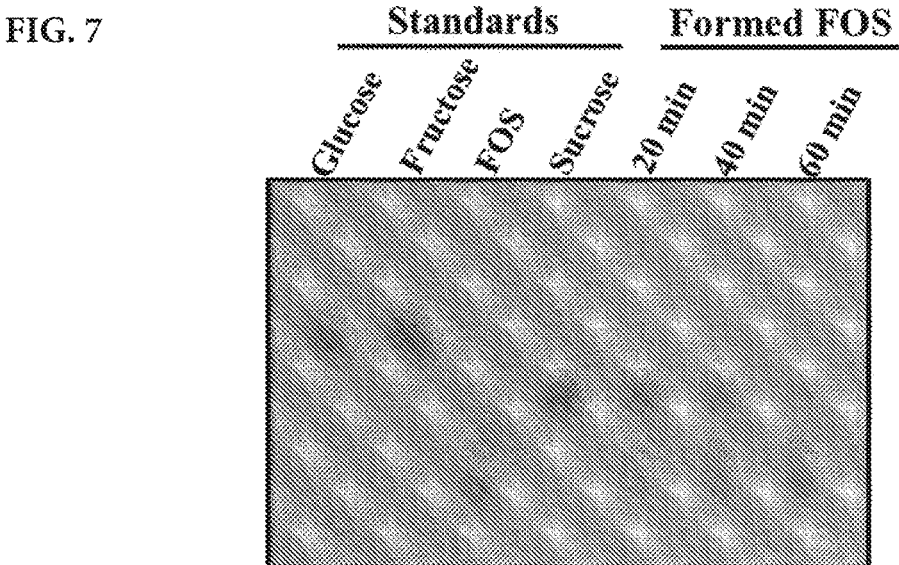
FIG. 7 depicts the generation of fructooligosaccharides (FOS) from sucrose and recombinant fructosyltransferase enzyme.

FIG. 7 depicts the TLC analysis done for the generation of fructooligosaccharides (FOS) from sucrose and recombinant fructosyltransferase enzyme.

The sample was further subjected to High Performance Liquid Chromatography (HPLC) for quantitative estimation of the production of fructooligosaccharides. The HPLC analysis was done using an amine column (Zorbax NH$_2$ column, Agilent Technologies) having 4.6 (ID)×150 mm (length) and 5 $\mu$m (particle size). The standard solutions of glucose, fructose, kestose, nystose, fructosylnystose and sucrose of different concentrations were run for generating standard curves.

Figure 8:
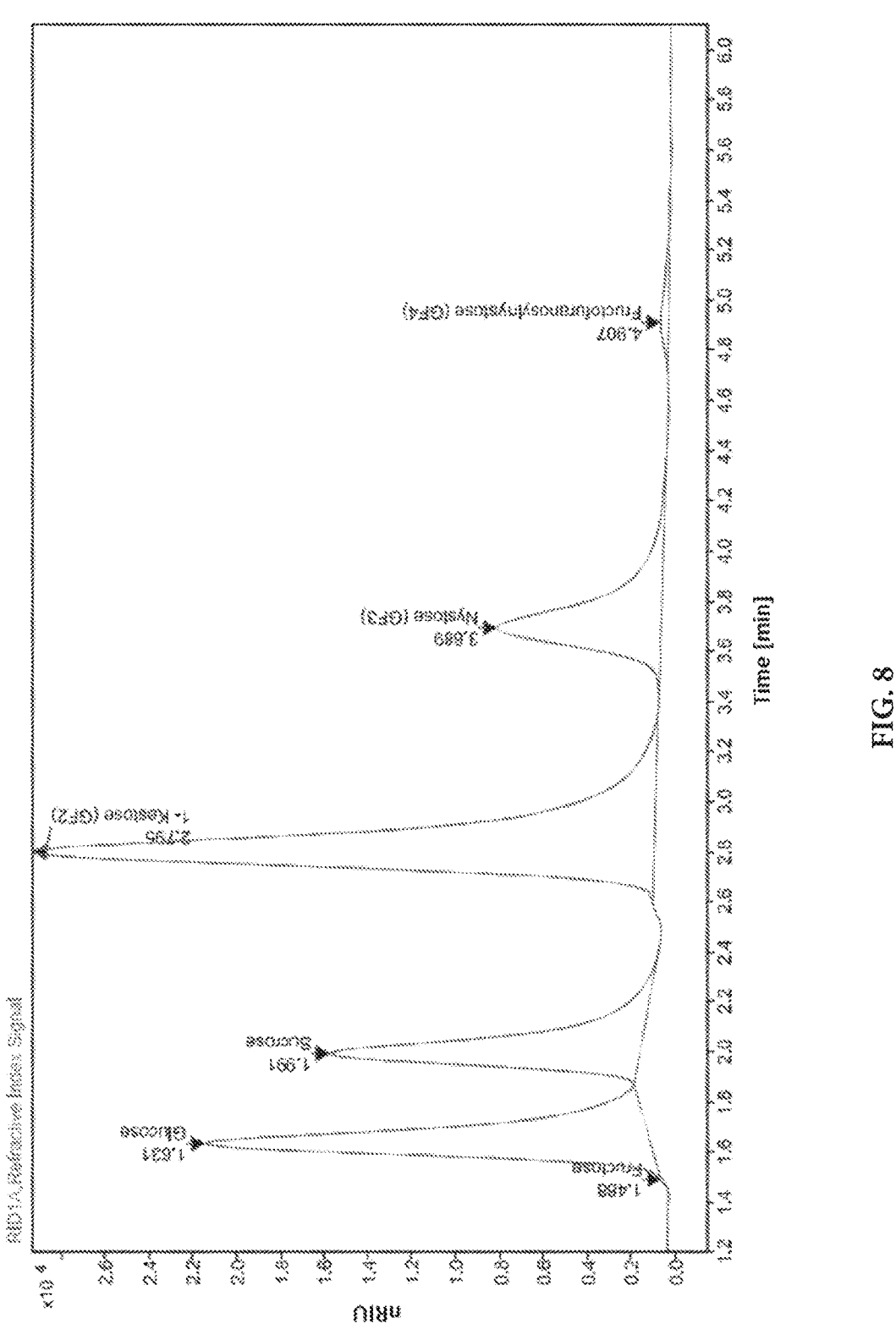
FIG. 8 depicts the HPLC analysis chromatogram of FOS samples.

FIG. 8 depicts the HPLC analysis chromatogram of FOS samples. Table 12 depicts the percentage of formation of fructooligosaccharides (FOS) and the recovered glucose, fructose and sucrose at the end of 60 min reaction time.

TABLE 12

The percentage of formation of fructooligosaccharides (FOS) and the recovered sucrose, glucose and fructose at the end of 120 min reaction time

| | 80% Sucrose substrate | On 100% Sucrose substrate basis |
|---|---|---|
| FOS (%) | 48.479 | 61.2484 |
| Sucrose (%) | 11.6875 | 14.7659 |
| Glucose (%) | 18.9842 | 23.9846 |
| Fructose (%) | 0.00081 | 0.0010 |

100 ml of 80% (w/v) sucrose solution was reacted with fructosyltransferase enzyme for the conversion of sucrose into FOS. The quantities of recovered FOS, sucrose, glucose, and fructose from the reaction after terminating the reaction by heat at the end of 60 min were measured and presented as 80% and 100% sucrose basis.

The studies demonstrated that the purified enzymes are able to effectively convert a very high amount of sugars into fructooligosaccharides.

Example 8: Characterization of Recombinant Fructosyltransferase of *Aspergillus japonicus*

The harvested fructosyltransferase of *Aspergillus japonicus* was characterized to identify bioactive fragments. It was found that following bioactive fragments of fructosyltransferase are conserved and accounts for the catalytic activities:

TABLE 13

Bioactive fragments of fructosyltransferase are conserved and accounts for the catalytic activities

| Position | Fragment | SEQ ID Number |
|---|---|---|
| 57-62 | QIGDPC | SEQ ID NO: 24 |
| 119-132 | DGAVIPVGVNNTPT | SEQ ID NO: 25 |
| 320-330 | SGLPIVPQVS | SEQ ID NO: 26 |
| 401-416 | GDQYEQADGFPTAQQG | SEQ ID NO: 27 |

It was further found that the following amino acids residues in fructosyltransferase of *Aspergillus japonicus* were involved in forming a hydrogen bond network around the catalytic triad. The hydrogen bond network is important for the stable stereochemistry around the catalytic triad:

Arg-190

Tyr-369

Glu-318

His-332

Asp-191

Thr-293

Asp-119

His-144

It was also found that the following hydrophobic residues in fructosyltransferase of *Aspergillus japonicus* take part in forming a negatively charged pocket around the active site:

Leu-78

Phe-118

Ala-370

Trp-398

Ile-143

Further, the following important residues of fructosyltransferase of *Aspergillus japonicus* that take part in interactions at the entrance of active pocket were identified:

Glu-405

His-332

Tyr-404

Conserved bioactive fragment of fructosyltransferase of *Aspergillus japonicus* (Position 57-62)

---

The invention claimed is:

1. A modified fructosyltransferase of *Aspergillus japonicus*, wherein the modification is a fusion of fructosyltransferase of *Aspergillus japonicus* having the amino acid sequence of SEQ ID NO: 1 to a signal peptide, wherein the signal peptide is alpha-factor of *Saccharomyces cerevisiae* (FAK), alpha-factor full of *S. cerevisiae* (FAKS), alpha factor_T of *S. cerevisiae* (AT), alpha-amylase of *Aspergillus niger* (AA), glucoamylase of *Aspergillus awamori* (GA), inulinase of *Kluyveromyces* maxianus (IN), invertase of *S. cerevisiae* (IV), killer protein of *S. cerevisiae* (KP), lysozyme of *Gallus gallus* (LZ), or serum albumin of *Homo sapiens* (SA).

2. The modified polypeptide as claimed in claim 1, wherein:
 a) FAK comprises the amino acid sequence of SEQ ID NO: 3;
 b) FAKS comprises the amino acid sequence of SEQ ID NO: 4;
 c) AT comprises the amino acid sequence of SEQ ID NO: 5;
 d) AA comprises the amino acid sequence of SEQ ID NO: 6;
 e) GA comprises the amino acid sequence of SEQ ID NO: 7;
 f) IN comprises the amino acid sequence of SEQ ID NO: 8;
 g) IV comprises the amino acid sequence of SEQ ID NO: 9;
 h) KP comprises the amino acid sequence of SEQ ID NO: 10;
 i) LZ comprises the amino acid sequence of SEQ ID NO: 11; and
 j) SA comprises the amino acid sequence of SEQ ID NO: 12;
and wherein the signal peptide enables the extracellular secretion of the modified polypeptide comprising the amino acid sequence of SEQ ID NO: 1.

3. A nucleic acid encoding the peptide as claimed in claim 1.

4. The nucleic acid as claimed in claim 3, wherein the nucleic acid comprises the sequence of SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, or SEQ ID NO: 22.

5. An expression vector comprising the nucleic acid as claimed in claim 3 operably linked to a promoter.

6. The expression vector as claimed in claim 5, wherein the promoter for fructosyltransferase gene is a promoter for the gene: alcohol oxidase 1 (AOX1), alcohol dehydrogenase (ADH3), dihydroxyacetone phosphatase (DAS), formaldehyde dehydrogenase (FLD1), L-rhamnonate dehydratase (LRA3), thiamine biosynthesis protein (THI11), glyceraldehyde-3-phosphate dehydrogenase (GAP), GTPase involved in secretion (YPT1), translation elongation factor-1 alpha (TEF1), glycosylphosphatidyl inositol (GCw14), or phosphoglycerate kinase (PGK1).

7. The expression vector as claimed in claim 5, wherein the expression vector is pPICZαA, pPICZαB, pPICZαC, pGAPZαA, pGAPZαB, pGAPZαC, pPIC3, pPIC3.5, pPIC3.5K, PA0815, pPIC9, pPIC9K, IL-D2, or pHIL-S1, and wherein the expression vector is configured for secretory or intracellular expression of fructosyltransferase from *Aspergillus japonicus* as set forth in SEQ ID NO: 1.

8. A recombinant *Pichia pastoris* host cell comprising the expression vector as claimed in claim 6.

9. The recombinant *Pichia pastoris* host cell as claimed in claim 8, wherein the host cell is *Pichia pastoris* Mut+, *Pichia pastoris* Mut S, *Pichia pastoris* Mut-, *Pichia pastoris* KM71H, *Pichia pastoris* KM71, *Pichia pastoris* SMD1168H, *Pichia pastoris* SMD1168, *Pichia pastoris* X33, or *Pichia pastoris* GS115.

10. A method of producing the recombinant *Pichia pastoris* host cell according to claim 8 capable of expressing fructosyltransferase of *Aspergillus japonicus* comprising the amino acid sequence of SEQ ID NO: 1, the process comprising the steps of:
 a) synthesizing a modified nucleic acid encoding fructosyltransferase from *Aspergillus japonicus* comprising the sequence as set forth in SEQ ID NO: 1;
 b) constructing a vector comprising the modified nucleic acid; and
 c) transforming a *Pichia pastoris* host cell with the vector of step (b) to obtain a recombinant *Pichia pastoris* host cell.

11. A process for expressing fructosyltransferase of *Aspergillus japonicus* comprising the sequence as set forth in SEQ ID NO: 1 according to claim 1, the process comprising:
 a) culturing recombinant *Pichia pastoris* host cells capable of expressing fructosyltransferase of *Aspergillus japonicus* comprising the sequence as set forth in SEQ ID NO: 1 in a suitable fermentation medium to obtain a fermentation broth;
 b) harvesting supernatant from the fermentation broth, wherein the supernatant contains recombinant fructosyltransferase; and
 c) purifying recombinant fructosyltransferase.

12. The process as claimed in claim 11, wherein the fermentation medium is Basal Salt Media.

13. The process as claimed in claim 11, wherein the pH of the fermentation broth is maintained in the range from 4.0 to 7.5.

14. The process as claimed in claim 11, wherein the temperature of the fermentation broth is maintained in the range from 15° C. to 45° C.

15. The modified polypeptide as claimed in claim 1 for use in the production of fructooligosaccharides.

* * * * *